US008518401B1

(12) United States Patent
Kuboi et al.

(10) Patent No.: US 8,518,401 B1
(45) Date of Patent: Aug. 27, 2013

(54) TREATING INFLAMMATORY DISEASES WITH ANTIBODIES THAT INHIBIT FRACTALKINE-CXCR1 INTERACTION

(75) Inventors: Yoshikazu Kuboi, Tsukuba (JP); Toshio Imai, Kobe (JP); Miyuki Nishimura, Kobe (JP); Keiko Mizuno, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 228 days.

(21) Appl. No.: 11/718,246

(22) PCT Filed: Oct. 31, 2005

(86) PCT No.: PCT/JP2005/020009
§ 371 (c)(1),
(2), (4) Date: Apr. 30, 2007

(87) PCT Pub. No.: WO2006/046739
PCT Pub. Date: May 4, 2006

(30) Foreign Application Priority Data

Oct. 29, 2004 (JP) .................................. 2004-316708
Jul. 15, 2005 (JP) .................................. 2005-206870

(51) Int. Cl.
*A61K 39/395* (2006.01)

(52) U.S. Cl.
USPC ..................... 424/130.1; 424/141.1; 514/885

(58) Field of Classification Search
None
See application file for complete search history.

(56) References Cited

U.S. PATENT DOCUMENTS

| | | | |
|---|---|---|---|
| 6,013,257 | A | 1/2000 | Pan |
| 6,096,312 | A | 8/2000 | Nakamura et al. |
| 6,180,377 | B1 | 1/2001 | Morgan et al. |
| 6,420,121 | B1 | 7/2002 | Nelson et al. |
| 6,548,654 | B1 | 4/2003 | Hardiman et al. |
| 6,566,503 | B2 | 5/2003 | Hardiman et al. |
| 7,115,379 | B1 | 10/2006 | Hardiman et al. |
| 7,431,924 | B2 | 10/2008 | Hardiman et al. |
| 7,585,502 | B2 | 9/2009 | Hardiman et al. |
| 7,785,804 | B2 | 8/2010 | Hardiman et al. |
| 2002/0055456 | A1 | 5/2002 | Koch |
| 2002/0192212 | A1 | 12/2002 | Imai et al. |
| 2003/0027990 | A1 | 2/2003 | Hardiman et al. |
| 2006/0233710 | A1 | 10/2006 | Matsushima et al. |
| 2006/0275297 | A1 | 12/2006 | Hardiman et al. |
| 2008/0063635 | A1 | 3/2008 | Takahashi et al. |
| 2009/0017032 | A1 | 1/2009 | Hardiman et al. |
| 2009/0317398 | A1 | 12/2009 | Hardiman et al. |

FOREIGN PATENT DOCUMENTS

| | | |
|---|---|---|
| EP | 1 520 586 | 4/2005 |
| JP | 7-509359 A | 10/1995 |
| JP | 2001-218581 | 8/2001 |
| JP | 2002 345454 | 12/2002 |
| WO | 94/01547 | 1/1994 |
| WO | 00 09511 | 2/2000 |
| WO | 01 60406 | 8/2001 |
| WO | WO 01/60406 A1 * | 8/2001 |
| WO | 02 076990 | 10/2002 |
| WO | 03 018549 | 3/2003 |
| WO | 2004/108895 A2 | 12/2004 |
| WO | 2005 032589 | 4/2005 |
| WO | 2005 033115 | 4/2005 |
| WO | WO 2006/107257 A1 | 10/2006 |
| WO | WO 2006/107258 A1 | 10/2006 |

OTHER PUBLICATIONS

Chuntharapai et al (1997) Methods in Enzymology, vol. 288, pp. 15-27.*
Sakurai et al (1995), J. Clin. Invest. 96:2357-2363.*
Atsushi Inoue, et al. "Antagonist of Fractalkine (CX3CL1) Delays the Initiation and Ameliorates the Progression of Lupus Nephritis in MRL/lpr Mice", Arthritis and Rheumatism, vol. 52, No. 5, May 2005, pp. 1522-1533.
Proceedings of the Japanese Society for Immunology, vol. 33, 2003 (corresponding to Journal of Immunology, vol. 273, No. 11, pp. 7010-7016, 2004; previously filed on Apr. 30, 2007.
Toshihiro Nanki, et al., "Inhibition of Fractalkine Ameliorates Murine Collagen-Induced Arthritis", The Journal of Immunology, vol. 173, No. 11, pp. 7010-7016, 2004.
Lili Feng, et al., Prevention of Crescentic Glomerulonephritis by Immunoneutralization of the Fractalkine Receptor CX3CR1, Rapid Communication, Kidney International, vol. 56, No. 2, pp. 612-620, 1999.
Ian N. Johnston, et al., "A Role for Proinflammatory Cytokines and Fractalkine in Analgesia, Tolerance, and Subsequent Pain Facilitation Induced by Chronic Intrathecal Morphine", The Journal of Neuroscience, vol. 24, No. 33, pp. 7353-7365, 2004.
Shizhong Chen, et al., In Vivo Inhibition of CC and CX3C Chemokine-Induced Leukocyte Infiltration and Attenuation of Glomerulonephritis in Wistar-Kyoto (WKY) Rats by vMIP-II, J. Exp. Med., vol. 188, No. 1, pp. 193-198, 1998.
Andreas Schaefer, et al., "Novel Role of the Membrane-Bound Chemokine Fractalkine in Platelet Activation and Adhesion", Blood, vol. 103, No. 2, pp. 407-412, 2004.
Violetta Zujovic, et al., "In Vivo Neutralization of Endogenous Brain Fractalkine Increases Hippocampal TNF Sigma and 8-Isoprostane Production Induced by Intracerebroventricular Injection of LPS", Journal of Neuroimmunology, vol. 115, pp. 135-143, 2001.
Andrew D. Lucas, et al., "The Transmembrane Form of the CX3CL1 Chemokine Fractalkine is Expressed Predominantly by Epithelial Cells in Vivo", American Journal of Pathology, vol. 158, No. 3, pp. 855-866, 2001.
Andreas Muehlhoefer, et al., "Fractalkine is an Epithelial and Endothelial Cell-Derived Chemoattractant for Intraepithelial Lymphocytes in the Small Intestinal Mucosa", The Journal of Immunology, vol. 164, pp. 3368-3376, 2000.
Lisa A. Robinson, et al., "A Role for Fractalkine and Its Receptor (CX3CR1) in Cardiac Allograft Rejection", The Journal of Immunology, vol. 165, pp. 6067-6072, 2000.
Leilani L. Santos, et al., "Suppression of Adjuvant Arthritis and Synovial Macrophage Inducible Nitric Oxide by N-Iminoethyl-L-Ornithine, a Nitric Oxide Synthase Inhibitor", Inflammation, vol. 21, No. 3, pp. 299-311, 1997.

(Continued)

*Primary Examiner* — Prema Mertz
(74) *Attorney, Agent, or Firm* — Oblon, Spivak, McClelland, Maier & Neustadt, L.L.P.

(57) ABSTRACT

A therapeutic agent for an inflammatory disease comprising an antibody or a CX3CR1 antagonist that inhibits an interaction of fractalkine and CX3CR1 is provided.

8 Claims, 25 Drawing Sheets

(56) References Cited

OTHER PUBLICATIONS

Toshihiro Nanki, et al. "Migration of CX3CR1-Positive T Cells Producing Type-1 Cytokines and Cytotoxic Molecules Into the Synovium of Patients With Rheumatoid Arthritis", Arthritis and Rheumatism, vol. 46, No. 11, Nov. 2002, pp. 2878-2883.
Takeshi Echigo, et al. "Expression of Fractalkine and Its Receptor, $CX_3CR1$, in Atopic Dermatitis: Possible Contribution to Skin Inflammation", The Journal of Allergy and Clinical Immunology, vol. 113, No. 5, May 2004, pp. 940-948.
Paolo Fraticelli, et al. "Fractalkine (CX3CL1) as an Amplification Circuit of Polarized Th1 Responses", The Journal of Clinical Investigation, vol. 107, No. 9, May 2001, pp. 1173-1181.
Gembu Imamura, et al. "Pharmacological Preconditioning With Resveratrol: An Insight With iNOS Knockout Mice", American Journal of Phisiology, vol. 282, No. 6, Jun. 2002 pp. H1996-H2003.
Yuji Naito, et al. "A Novel Potent Inhibitor of Inducible Nitric Oxide Inhibitor, ONO-1714, Reduces Intestinal Ischemia-Reperfusion Injury in Rats", Nitric Oxide, vol. 10, 2004, pp. 170-177.
Philipp Lirk, et al. "Inducible Nitric Oxide Synthase-Time for Reappraisal", Current Drug Targets-Inflammation and Allergy, vol. 1, No. 1, 2002, pp. 89-108.
Betty Poon, et al. "Complexity of Inducible Nitric Oxide Synthase Cellular Source Determines Benefit Versus Toxicity", Circulation, vol. 108, No. 9, Sep. 2, 2003, pp. 11071112.
Anne-Cecile Rimaniol, et al. "The $CX_3C$ Chemokine Fractalkine in Allergic Asthma and Rhinitis". The Journal of Allergy and Clinical Immunology, vol. 112, No. 6, Dec. 2003, pp. 1139-1146.
David H. McDermott, et al. "Chemokine Receptor Mutant CX3CR1-M280 has Impaired Adhesive Function and Correlates With Protection From Cardiovascular Disease in Humans", The Journal of Clinical Investigation, vol. 111, No. 8, Apr. 2003, pp. 1241-1250.
G. CH. Beck, et al. "Release of CXC-Chemokines by Human Lung Microvascular Endothelial Cells (LMVEC) Compared With Macrovascular Umbilical Vein Endothelial Cells", Clinical and Experimental Immunology, vol. 118, No. 2, Nov. 1999, pp. 298-303.
Christophe Combadiere, et al. "Decreased Atherosclerotic Lesion Formation in CX3CR1/Apolipoprotein E Double Knockout Mice", Circulation, vol. 107, No. 7, Feb. 25, 2003, pp. 1009-1016.
Sulpicio G. Soriano, et al. "Mice Deficient in Fractalkine Are Less Susceptible to Cerebral Ischemia-reperfusion Injury", Journal of Neuroimmunology, vol. 125, Apr. 2002, pp. 59-65.
Christopher A. Haskell, et al. "Targeted Deletion of $CX_3CR1$ Reveals a Role for Fractalkine in Cardiac Allograft Rejection", The Journal of Clinical Investigation, vol. 108, No. 5, Sep. 2001, pp. 679-688.
Natalya Serbina, et al. "TNF/iNOS-Producing Dendritic Cells Mediate Innate Immune Defense Against Bacterial Infection", Immunity, vol. 19, No. 1, Jul. 2003, pp. 59-70.
Frederic Geissmann, et al. "Blood Monocytes Consist of Two Principal Subsets With Distinct Migratory Properties", Immunity, vol. 19, No. 1, Jul. 2003, pp. 71-82.
Petronela Ancuta, et al. "Fractalkine Preferentially Mediates Arrest and Migration of CD16+ Monocytes", The Journal of Experimental Medicine, vol. 197, No. 12, Jun. 16, 2003, pp. 1701-1707.
Salvatore Cuzzocrea, et al. "Beneficial Effects of GW274150, a Novel, Potent and Selective Inhibitor of iNOS Activity, in a Rodent Model of Collagen-Induced Arthritis", European Journal of Pharmacology, vol. 453, No. 1, Oct. 18, 2002, pp. 119-129.
Jean-Pierre Pelletier, et al. "Reduced Progression of Experimental Osteoarthritis in Vivo by Selective Inhibition of Inducibles Nitric Oxide Synthase", Arthritis and Rheumatism, vol. 41, No. 7, Jul. 1998, pp. 1275-1286.
Esko Kankuri, et al. "Suppression of Acute Experimental Colitis by a Highly Selective Inducible Nitric-Oxide Synthase Inhibitor, N-[3-(Aminomethyl)Benzyl]acetamidine", Journal of Pharmacology and Experimental Therapeutics, vol. 298, No. 3, Sep. 2001, pp. 1128-1132.
Yuji Naito, et al. "The Inducible Nitric Oxide Synthase Inhibitor ONO-1714 Blunts Dextran Sulfate Sodium Colitis in Mice", The European Journal of Pharmacology, vol. 412, 2001, pp. 91-99.
Gabriele Sass, et al. "Inducible Nitric Oxide Synthase is Critical for Immune-Mediated Liver Injury in Mice", Journal of Clinical Investigation, vol. 107 No. 4, Feb. 2001, pp. 439-447.
Mark A. Birrell, et al. Pharmacological Assessment of the Nitric-Oxide Synthase Isoform Involved in Eosinophilic Inflammation in a Rat Model of Sephadex-Induced Airway Inflammation,The Journal of Pharmacology and Experimental Therapeutics, vol. 304. No. 3, Mar. 2003, pp. 1285-1291.
Katsuya Mikawa, et al. ONO-1714, A Nitric Oxide Synthase Inhibitor, Attenuates Endotoxin-Induced Acute Lung Injury in Rabbits, Anesthesia and Analgesia, vol. 97, No. 6, Dec. 2003 pp. 1751-1755.
Ingrid H.C. Vos, et al. "Inhibition of Inducible Nitric Oxide Synthase Improves Graft Function and Reduces Tubuloiterstitial Injury in Renal Allograft Rejection", European Journal of Pharmacology vol. 391, Nos. 1/2, Mar. 10, 2000, pp. 31-38.
Sophie Parmentier, et al. "Selective Inhibition of Inducible Nitric Oxide Synthase Prevents Ischaemic Brain Injury", British Journal of Pharmacology, vol. 127, No. 2, May 1999, pp. 546-552.
Proceedings of the Japanese Society for Immunology, vol. 33, 2003 (corresponding to Journal of Immunology, vol. 173, No. 11, 2004; previosly filed on Jun. 4, 2007).
Sans M. et al., "AGA Abstracts T1786-W1189", Gastroenterology, vol. 126, No. 4, XP-022471378, Apr. 1, 2004, pp. A512-A585.
Daniele D'Ambrosio, et al., "Chemokine receptors in inflammation: an overview", Journal of Immunological Methods, vol. 273, No. 1-2, XP-004402136, Feb. 1, 2003, pp. 3-13.
Hisanori Umehara, et al., "Fractalkine and vascular injury", Trends in immunology, vol. 22, No. 11, XP-004319768, Nov. 1, 2001, pp. 602-607.
David R. Greaves, et al., "Inflammation and immune responses in atherosclerosis", TRENDS in Immunology, vol. 23, No. 11, XP-004388299, Nov. 1, 2002, pp. 535-541.
Jeffrey H. Ruth, et al., "Fractalkine, a Novel Chemokine in Rheumatoid Arthritis and in Rat Adjuvant-Induced Arthritis", Arthritis & Rheumatism, vol. 44, No. 7, Jul. 2001, pp. 1568-1581.
Takashi Namekawa, et al., "Functional Subsets of CD4 T Cells in Rheumatoid Synovitis", Arthritis & Rheumatism, vol. 41, No. 12, Dec. 1998, pp. 2108-2116.
Brian W.C. Wong, et al., "Characterization of fractalkine (CX3CL1) and CX3CR1 in human coronary arteries with native atherosclerosis, diabetes mellitus, and transplant vascular disease", Cardiovascular Pathology, vol. 11, 2002, pp. 332-338.
Toshio Imai, et al, "Identification and Molecular Characterization of Fractalkine Receptor $CX_3CR1$, which Mediates Both Leukocyte Migration and Adhesion", Cell., vol. 91, No. 4, 1997, pp. 521-530.
Dorland's Illustrated Medical Dictionary, $27^{th}$ Edition, 1998, pp. 1089 and 1460.
Hakan Goker, et al., "Acute graft-vs-host disease: Pathobiology and management", Experimental Hematology, vol. 29, 2001, pp. 259-277.
FASEB Journal, Meeting Abstracts, vol. 16, No. 4, 2002, p. A691.
Miquel Sans, et al., "Enhanced Recruitment of CX3CR1+ T Cells by Mucosal Endothelial Cell-Derived Fractalkine in Inflammatory Bowel Disease", Gastroenterology, vol. 132, 2007, pp. 139-153.
Carol J. Raport, et al., "The orphan G-protein-coupled receptor-encoding gene *V28* is closely related to genes for chemokine receptors and is expressed in lymphoid and neural tissues", Gene, vol. 163, 1995, pp. 295-299.
Athanasios Dagkalis, et al., "CX3CR1-deficiency is associated with increased severity of disease in experimental autoimmune uveitis", Immunology, vol. 128, 2009. pp. 25-33.
Taku Kobayashi, et al., "Exclusive Increase of $CX3CR1^+ CD28^- CD4^+$ T Cells in Inflammatory Bowel Disease and Their Recruitment as Intraepithelial Lymphocytes", Inflamm. Bowel Dis., vol. 13, 2007, pp. 837-846.
Interferon Cytokine Research, vol. 19, Suppl. 1, 1999, p. S139.
David M. Hoover, et al., "The Crystal Structure of the Chemokine Domain of Fractalkine Shows a Novel Quaternary Arrangement", Journal of Biol. Chem., vol. 275, No. 30, 2000, pp. 23187-23193.
Masako Murai, et al., "Active participation of $CCR5^+CD8^+$ T lymphocytes in the pathogenesis of liver injury in graft-versus-host disease", Journal of Clinical Investigation, vol. 104, 1999, pp. 49-57.

Francis V. Chisari, "Cytotoxic T Cells and Viral Hepatitis", Journal of Clinical Investigation, vol. 99, 1997, pp. 1472-1477.

Andreas R. Kammer, et al., "Molecular Mimicry of Human Cytochrome P450 by Hepatitis C Virus at the Level of Cytotoxic T Cell Recognition", J. Exp. Med., vol. 190, 1999, pp. 169-176.

M. Nagata, et al., "Evidence for the Role of CD8+ Cytotoxic T Cells in the Destruction of Pancreatic β-Cells in Nonobese Diabetic Mice", J. Immunol., vol. 152, 1994, pp. 2042-2050.

Miyuki Nishimura, et al., "Dual Functions of Fractalkine/CX3C Ligand 1 in Trafficking of Perforin+ /Granzyme B+ Cytotoxic Effector Lymphocytes That are Defined by CX3CR1 Expression", J. of Immunol., vol. 168, 2002, pp. 6173-6180.

Osamu Yoneda, et al., "Fractalkine-Mediated Endothelial Cell Injury by NK Cells", J. of Immunol., vol. 164, 2000, pp. 4055-4062.

Falko R. Fischer, et al., "Modulation of experimental autoimmune encephalomyelitis: effect of altered peptide ligand on chemokine and chemokine receptor expression", J. of Neuroimmunol., vol. 110, 2000, pp. 195-208.

Osamu Yoneda, et al., "Effects of fractalkine on NK cell activity and NK cell-mediated damage of endothelial cells", J. Osaka Odontol. Soc., vol. 62, No. 2, 1999, pp. 90-97 (With English Abstract).

Satoshi Ueha, et al., "Intervention of MAdCAM-1 or fractalkine alleviates graft-versus-host reaction associated intestinal injury while preserving graft-versus-tumor effects". Journal of Leukocyte Biology, vol. 81, No. 1, 2007, pp. 176-185.

Georg F. Belke-Louis, et al., "μ-Opioid Receptor Expression in High Five™ Insect Cells is Regulated by 5' Untranslated Region (5'UTR)", Life Sciences, vol. 64, No. 11, 1999, pp. 913-921.

The Japanese Biochemical Society, ed., "Sin-Seikagaku Jikken Koza (New Lecture of Biochemical Experiment) 12, Molecular Immunology III -antigen, antibody, complement-", 1st Ed., 1992, pp. 3-6.

Ailsa M. Campbell, "General properties and applications of monoclonal antibodies", Chapter 1, Monoclonal Antibody Technology, 1985, pp. 1-32.

Masako Murai, et al., "Peyer's patch is the essential site in initiating murine acute and lethal graft-versus-host reaction", Nature Immunology, vol. 4, No. 2, Feb. 2003, pp. 154-160.

Diane Berangere RE, et al., "Fractalkine: moving from chemotaxis to neuroprotection", Nature Neuroscience, vol. 9, 2006, pp. 859-861.

Astrid E. Cardona, et al., "Control of microglial neurotoxicity by the fractalkine receptor", Nature Neuroscience, vol. 9, 2006, pp. 917-924.

Gillian M. Griffiths, et al., "Perforin and granzyme A expression identifying cytolytic lymphocytes in rheumatoid arthritis", Proc. Natl. Acad. Sci. USA, vol. 89, 1992, pp. 549-553.

Jeffrey K. Harrison, et al., "Role for neuronally derived fractalkine in mediating interactions between neurons and CX3CR1-expressing microglia", Proc. Nat. Acad. Sci. USA, vol. 95, 1998, pp. 10896-10901.

Miyuki Nishimura, et al., "Analysis of fractalkine receptor, CX3CR1, selectively expressed on effector killer lymphocytes", Proceedings of the Japanese Society for Immunology, vol. 30, 2000, p. 192, 2-F-270-P/O (With English Translation).

Clark F. Ford, et al., "Fusion Tails for the Recovery and Purification of Recombinant Proteins", Protein Expression and Purification, vol. 2, No. 2-3, 1991, pp. 95-107.

Cedric Auffray, et al., "Monitoring of Blood Vessels and Tissues by a Population of Monocytes with Patrolling Behavior", Science, vol. 317, 2007, pp. 666-670.

Jan Hendrik Niess, et al., "CX$_3$CR1-Mediated Dendritic Cell Access to the Intestinal Lumen and Bacte . . . ", Science, vol. 307, 2005, pp. 254-258.

Jing Chen, et al., "Overstaying their welcome: defective CX3CR1 microglia eyed in macular degeneration", The Journal of Clinical Investigation, vol. 117, 2007, pp. 2758-2762.

Christophe Combadiere, et al., "CX3CR1-dependent subretinal microglia cell accumulation is associated with cardinal features of age-related macular degeneration", The Journal of Clinical Investigation, vol. 117, 2007, pp. 2920-2928.

Hisanori Umehara, et al., "Fractalkine in Vascular Biology From Basic Rsearch to Clinical Disease", Thromb. Vasc. Biol., vol. 24, 2004, pp. 34-40.

Ryuzo Kawamori, et al., "Diabetes Chiryo (Treatment) [Step:2] to Avoid Drop Out", Chiryo, vol. 80, No. 12, 1998, pp. 92-98.

Gembu Imamura, et al. "Pharmacological Preconditioning With Resveratrol: An Insight With iNOS Knockout Mice", American Journal of Physiology, vol. 282, No. 6, Jun. 2002 pp. H1996-H2003.

Yuji Naito, et al. "A Novel Potent Inhibitor of Inducible Nitric Oxide Inhibitor, ONO-1714, Reduces Intestinal Ischemia-Reperfusion Injury in Rats", Nitric Oxide, vol. 10, No. 3, 2004, pp. 170-177.

Betty Poon, et al. "Complexity of Inducible Nitric Oxide Synthase Cellular Source Determines Benefit Versus Toxicity", Circulation, vol. 108, No. 9, Sep. 2, 2003, pp. 1107-1112.

Anne-Cecile Rimaniol, et al. "The CX$_3$C Chemokine Fractalkine in Allergic Asthma and Rhinitis", The Journal of Allergy and Clinical Immunology, vol. 112, No. 6, Dec. 2003, pp. 1139-1146.

* cited by examiner

Control antibody

Anti-fractalkine antibody (5H8-4)

Control antibody

Anti-fractalkine antibody (5H8-4)    x10

Control antibody

Anti-fractalkine antibody (5H8-4)

Negative control

SEQUENCE LISTING

<160> NUMBER OF SEQ ID NOS: 129

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agctgaactt gagcgaggag                                            20

<210> SEQ ID NO 2
<211> LENGTH: 20
<212> TYPE: DNA
<213> ORGANISM: Artificial Sequence
<220> FEATURE:

<223> OTHER INFORMATION: primer

<400> SEQUENCE: 2
tgccccatag gaaaagactg                                                 20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggcaagatga cctcacgaat                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctgtgtcgtc tccaggacaa                                                 20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gctttaacag caggccagac                                                 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggaagcacca ggtgtcaagt                                                 20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ccagtgtggg aagctgtctt                                                 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aagcaaaaga ggaggcaaca                                                 20

<210> SEQ ID NO 9

```
<211> LENGTH: 20
<212> TYPE: DNA
<213> ORGANISM: Artificial Sequence
<220> FEATURE:
<223> OTHER INFORMATION: primer

<400> SEQUENCE: 9
ggcattttga acgaggtcac                                                20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aaatatgcga agcaccttgg                                                20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tgcaagcaga agcacaagtt                                                20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgtgtgttca ctgggaagga                                                20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccatcgtccc tagagctgag                                                20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gctggtcctt gtgaatggat                                                20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
```
ctgtggctac cggtggtatt                                                    20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gttctgccag ttccttctgc                                                    20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ggagacagga tgaccctgaa                                                    20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ttcagcaatt ctcgggatgt                                                    20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
aggtccctgt catgcttctg                                                    20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tcattgggat catcttgctg                                                    20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
cttgaaggtg ttgccctcag                                                    20

<210> SEQ ID NO 22
<211> LENGTH: 20
<212> TYPE: DNA
<213> ORGANISM: Artificial Sequence
<220> FEATURE:

```
<223> OTHER INFORMATION: primer

<400> SEQUENCE: 22
tggggacacc ttttagcatc                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tccagagctt gagtgtgacg                                              20

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gccttgcctt tgttcagtat c                                            21

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
tgaatccgga atctaagacc a                                            21

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gaggctctct gctgtccatc                                              20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
accatgacac tctgcaacca                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gatgaattgg cgtggaatct                                              20

<210> SEQ ID NO 29
```

```
<211> LENGTH: 20
<212> TYPE: DNA
<213> ORGANISM: Artificial Sequence
<220> FEATURE:
<223> OTHER INFORMATION: primer

<400> SEQUENCE: 29
cccacttcct gctgtttctc                                                   20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ctcactgggg ttagcacaga                                                   20

<210> SEQ ID NO 31
<211> LENGTH: 20
<212> TYPE: PRT
<213> ORGANISM: Oryctolagus cuniculus

<400> SEQUENCE: 31

Cys Ser Ile Leu Ser Ser Phe Thr His Tyr Thr Ser Glu Gly Asp Gly
1               5                   10                  15

Ser Leu Leu Leu
            20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
gggctgtggc agtgtctact                                                   20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ctggttcacc cctctggata                                                   20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tgcctccctg actttcaaat                                                   20

<210> SEQ ID NO 35
<211> LENGTH: 20
<212> TYPE: DNA
<213> ORGANISM: Artificial Sequence
<220> FEATURE:
<223> OTHER INFORMATION: primer
```

<400> SEQUENCE: 35
tggcattgct gtatctgctc                                                  20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gggaagctaa agctcaccaa                                                  20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
cctctggctc tccatcattc                                                  20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
cttatcgtgg gcagctcagt                                                  20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ccatttgctt cctccaacat                                                  20

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
cgacttcttc aagtgactcc ttc                                              23

<210> SEQ ID NO 41
<211> LENGTH: 18
<212> TYPE: DNA
<213> ORGANISM: Artificial Sequence
<220> FEATURE:
<223> OTHER INFORMATION: primer

<400> SEQUENCE: 41
ctacgtcccg gtggatgc                                                    18

<210> SEQ ID NO 42
<211> LENGTH: 20
<212> TYPE: DNA

```
<213> ORGANISM: Artificial Sequence
<220> FEATURE:
<223> OTHER INFORMATION: primer

<400> SEQUENCE: 42
gatggatttt gcgttgctct                                              20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gtccagagta gtggggcaga                                              20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
gctgaaagct ctccacctca                                              20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
aggccacagg tattttgtcg                                              20

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
caaagccaga gtccttcaga g                                            21

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
gccactcctt ctgtgactcc                                              20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gccaggtgtc ttagccagtc                                              20
```

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
tcttcaatgt gctggtttgg                                        20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
atccagcgca agaaagaaaa                                        20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
aatagcgatc ctgagcttgc                                        20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
caacagccag ttctgcttgc                                        20

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
gatcctctgg ctggaggag                                         19

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
tccagaaggc cctcagacta                                        20

<210> SEQ ID NO 55
<211> LENGTH: 20
<212> TYPE: DNA
<213> ORGANISM: Artificial Sequence
<220> FEATURE:
<223> OTHER INFORMATION: primer -continued

```
<400> SEQUENCE: 55
tgagcttccc agatcacaga                                               20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
catttgcaca cctcaccatc                                               20

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
tccgttgctt aacgtcatgt                                               20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
cttgaaggtg ttgccctcag                                               20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tggggacacc ttttagcatc                                               20

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
tccagagctt gagtgtgacg                                               20

<210> SEQ ID NO 61
<211> LENGTH: 21
<212> TYPE: DNA
<213> ORGANISM: Artificial Sequence
<220> FEATURE:
<223> OTHER INFORMATION: primer

<400> SEQUENCE: 61
gccttgcctt tgttcagtat c                                             21

<210> SEQ ID NO 62
<211> LENGTH: 20
<212> TYPE: DNA
```

```
<213> ORGANISM: Artificial Sequence
<220> FEATURE:
<223> OTHER INFORMATION: primer

<400> SEQUENCE: 62
aggtccctgt catgcttctg                                               20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
tcattgggat catcttgctg                                               20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
ctgctttcag catccaagtg                                               20

<210> SEQ ID NO 65
<211> LENGTH: 19
<212> TYPE: DNA
<213> ORGANISM: Artificial Sequence
<220> FEATURE:
<223> OTHER INFORMATION: primer

<400> SEQUENCE: 65
cccagggaca ccgactact                                                19

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gctcacaaac agcgtcgtag                                               20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
agggcatgcc agagctataa                                               20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
ctttgcaact gcctctttcc                                               20
```

```
<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ttcccaggaa gaggttgaga                                               20

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
accatgacac tctgcaacca                                               20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
gatgaattgg cgtggaatct                                               20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
cccacttcct gctgtttctc                                               20

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ctcactgggg ttagcacaga                                               20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
gccagaggag gtgagacatc                                               20

<210> SEQ ID NO 75
<211> LENGTH: 20
<212> TYPE: DNA
<213> ORGANISM: Artificial Sequence
<220> FEATURE:
<223> OTHER INFORMATION: primer
```

<400> SEQUENCE: 75
gccagaggag gtgagacatc					20

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
tgcttctggg gactttctg					20

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
catccctgga acactccact					20

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
ttcttgctgt ggcaattcag					20

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
gcaggatttt gaggtccaga					20

<210> SEQ ID NO 80
<211> LENGTH: 22
<212> TYPE: DNA
<213> ORGANISM: Artificial Sequence
<220> FEATURE:
<223> OTHER INFORMATION: primer

<400> SEQUENCE: 80
tgtcctcagg atcactttca ga				22

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
agcaggagaa gccaatgaga					20

<210> SEQ ID NO 82
<211> LENGTH: 21
<212> TYPE: DNA

```
<213> ORGANISM: Artificial Sequence
<220> FEATURE:
<223> OTHER INFORMATION: primer

<400> SEQUENCE: 82
tgaatccgga atctaagacc a                                              21

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
gaggctctct gctgtccatc                                                20

<210> SEQ ID NO 84
<211> LENGTH: 19
<212> TYPE: DNA
<213> ORGANISM: Artificial Sequence
<220> FEATURE:
<223> OTHER INFORMATION: primer

<400> SEQUENCE: 84
caagcaagct cgcctcata                                                 19

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
gcatgttcca agacagcaga                                                20

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
gttctgctgg tctccagagg                                                20

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
tgccaccacc actaccacta                                                20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
gtcggcttct tctccaatca                                                20
```

```
<210> SEQ ID NO 89
<211> LENGTH: 19
<212> TYPE: DNA
<213> ORGANISM: Artificial Sequence
<220> FEATURE:
<223> OTHER INFORMATION: primer

<400> SEQUENCE: 89
gcatccggga ctttaaacc                                              19

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
tggatctgtg cttttttgctg                                            20

<210> SEQ ID NO 91
<211> LENGTH: 21
<212> TYPE: DNA
<213> ORGANISM: Artificial Sequence
<220> FEATURE:
<223> OTHER INFORMATION: primer

<400> SEQUENCE: 91
ccttctcctt tgttgcatct c                                           21

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
gctgaacaga ccgtcttcct                                             20

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
gtttgcagag ccagggtagt                                             20

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
ttcagcaaaa ccaaatgcag                                             20

<210> SEQ ID NO 95
<211> LENGTH: 22
<212> TYPE: DNA
<213> ORGANISM: Artificial Sequence
<220> FEATURE:
<223> OTHER INFORMATION: primer
```

```
<400> SEQUENCE: 95
tgcacttctt atttcaggca aa                                          22

<210> SEQ ID NO 96
<211> LENGTH: 20
<212> TYPE: DNA
<213> ORGANISM: Artificial Sequence
<220> FEATURE:
<223> OTHER INFORMATION: primer

<400> SEQUENCE: 96
tctacacctg cgtggttcag                                             20

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
gccaacacag aagatgatga ag                                          22

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98 tagggcttc acttctctgc                                              20

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
ccaaagagct cgtagcatcc                                             20

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
ccaaccggta ccttgctatg                                             20

<210> SEQ ID NO 101
<211> LENGTH: 20
<212> TYPE: DNA
<213> ORGANISM: Artificial Sequence
<220> FEATURE:
<223> OTHER INFORMATION: primer

<400> SEQUENCE: 101
gtgccacata ccaactggag                                             20

<210> SEQ ID NO 102
<211> LENGTH: 20
<212> TYPE: DNA
```

```
<213> ORGANISM: Artificial Sequence
<220> FEATURE:
<223> OTHER INFORMATION: primer

<400> SEQUENCE: 102
ccaagctcag cacacagaaa                                              20

<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103
tcagaatcac gctgagcatt                                              20

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
cccctgatgt ccagcaagta                                              20

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
tgcgatgagc ttagggaaac                                              20

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
agacgacata gacggcatcc                                              20

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
gtggttcagt tgtggtggtg                                              20

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
ctgggaagga atccctgaat                                              20
```

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
ctgggaagga atccctgaat                                               20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
gctgaaagct ctccacctca                                               20

<210> SEQ ID NO 111
<211> LENGTH: 20
<212> TYPE: DNA
<213> ORGANISM: Artificial Sequence
<220> FEATURE:
<223> OTHER INFORMATION: primer

<400> SEQUENCE: 111
aggccacagg tattttgtcg                                               20

<210> SEQ ID NO 112
<211> LENGTH: 21
<212> TYPE: DNA
<213> ORGANISM: Artificial Sequence
<220> FEATURE:
<223> OTHER INFORMATION: primer

<400> SEQUENCE: 112
caaagccaga gtccttcaga g                                             21

<210> SEQ ID NO 113
<211> LENGTH: 20
<212> TYPE: DNA
<213> ORGANISM: Artificial Sequence
<220> FEATURE:
<223> OTHER INFORMATION: primer

<400> SEQUENCE: 113
gccactcctt ctgtgactcc                                               20

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
gatggatttt gcgttgctct                                               20

<210> SEQ ID NO 115
<211> LENGTH: 20
<212> TYPE: DNA
<213> ORGANISM: Artificial Sequence
<220> FEATURE:
<223> OTHER INFORMATION: primer

```
<400> SEQUENCE: 115
gtccagagta gtggggcaga                                              20

<210> SEQ ID NO 116
<211> LENGTH: 20
<212> TYPE: DNA
<213> ORGANISM: Artificial Sequence
<220> FEATURE:
<223> OTHER INFORMATION: primer

<400> SEQUENCE: 116
cttgaaggtg ttgccctcag                                              20

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
tggggacacc ttttagcatc                                              20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
tccagagctt gagtgtgacg                                              20

<210> SEQ ID NO 119
<211> LENGTH: 21
<212> TYPE: DNA
<213> ORGANISM: Artificial Sequence
<220> FEATURE:
<223> OTHER INFORMATION: primer

<400> SEQUENCE: 119
gccttgcctt tgttcagtat c                                            21

<210> SEQ ID NO 120
<211> LENGTH: 19
<212> TYPE: DNA
<213> ORGANISM: Artificial Sequence
<220> FEATURE:
<223> OTHER INFORMATION: primer

<400> SEQUENCE: 120
ggtccctgtc atgcttctg                                               19

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
tcattgggat catcttgctg                                              20

<210> SEQ ID NO 122
<211> LENGTH: 20
<212> TYPE: DNA
```

```
<213> ORGANISM: Artificial Sequence
<220> FEATURE:
<223> OTHER INFORMATION: primer

<400> SEQUENCE: 122
accatgacac tctgcaacca                                              20

<210> SEQ ID NO 123
<211> LENGTH: 20
<212> TYPE: DNA
<213> ORGANISM: Artificial Sequence
<220> FEATURE:
<223> OTHER INFORMATION: primer

<400> SEQUENCE: 123
gatgaattgg cgtggaatct                                              20

<210> SEQ ID NO 124
<211> LENGTH: 20
<212> TYPE: DNA
<213> ORGANISM: Artificial Sequence
<220> FEATURE:
<223> OTHER INFORMATION: primer

<400> SEQUENCE: 124
cccacttcct gctgtttctc                                              20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
ctcactgggg ttagcacaga                                              20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
ctgctttcag catccaagtg                                              20

<210> SEQ ID NO 127
<211> LENGTH: 19
<212> TYPE: DNA
<213> ORGANISM: Artificial Sequence
<220> FEATURE:
<223> OTHER INFORMATION: primer

<400> SEQUENCE: 127
cccagggaca ccgactact                                               19

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
gctcacaaac agcgtcgtag                                              20
```

```
<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
agggcatgcc agagctataa                                              20
```

TREATING INFLAMMATORY DISEASES WITH ANTIBODIES THAT INHIBIT FRACTALKINE-CXCR1 INTERACTION

TECHNICAL FIELD

The present invention relates to a therapeutic agent for an inflammatory disease.

BACKGROUND ART

Chemokines are major cell migration factors in the living bodies and regulate lymphocyte infiltration into tissues via increase of cell motility and activation of cell adhesion molecules. Chemokines are classified into four subfamilies of CC, CXC, C and CXXXC on the basis of the sequence types of the first two cysteine residues. The members of the CC, CXC and C chemokine subfamilies are secretory proteins consisting of about 70 amino acids, and although they do not have activity as adhesion molecules themselves, they can induce cell adhesion. A secreted chemokine binds to a seven-transmembrane receptor on the surface of a target cell and activates integrin via the trimer G protein to induce cell adhesion or migration.

Recently, a novel simple lymphocyte infiltration mechanism was identified in addition to the known cell migration mechanism. This mechanism is mediated by fractalkine expressed on activated endothelial cells and a seven-transmembrane receptor, CX3CR1, expressed in monocytes, NK cells and a part of T cells in the blood flow. Fractalkine is the only member of the CXXXC chemokine subfamily and has distinct characteristics in the structure and functions thereof that are not found in other chemokines. Fractalkine is expressed on a cell surface as a membrane-bound protein having a chemokine domain, mucin domain, transmembrane domain and intracytoplasmic domain. The membrane-bound fractalkine by itself can mediate strong adhesion by binding to CX3CR1 even in the presence of a physiological blood flow rate without mediation of selectin or integrin. That is, by a one-stage reaction, the fractalkine-CX3CR1 cell infiltration system mediates a function similar to that of the multistage cell infiltration mechanism via selectin or integrin. Further, secretory fractalkine secreted from membrane-bound fractalkine by shedding binds to CX3CR1 and induces integrin activation and cell migration like the known chemokines.

Further, expression of fractalkine is induced when vascular endothelial cells are treated with inflammatory cytokines such as TNF and IL-1. On the other hand, CX3CR1 is expressed in monocytes, most of NK cells and a part of T cells, but not in neutrophils. Therefore, the fractalkine-CX3CR1 cell infiltration system appears to be a very efficient mechanism for mobilizing certain types of immunocytes onto endothelial cells of damaged tissues or into the tissues. Since fractalkine is induced on vascular endothelial cells upon inflammation, and CX3CR1 exists in many types of leukocytes as described above, it is strongly suggested that the fractalkine-CX3CR1 cell infiltration system is involved in development and progression of pathological conditions in inflammatory diseases. In fact, many reports have been made on involvement of the fractalkine-CX3CR1 cell infiltration system in inflammatory diseases, and such reports have been made on many diseases such as rheumatoid arthritis (Non-patent document 1), inflammatory bowel diseases of which typical examples are ulcerative colitis and Crohn's disease (Non-patent document 2), psoriasis and atopic dermatitis (Non-patent documents 3 and 4), asthma (Non-patent document 5), arteriosclerosis (Non-patent document 6), acute respiratory distress syndrome (Non-patent document 7), and so forth. Further, effects of preventing progression of pathological conditions and improving the conditions can be expected to be provided by inhibition of the fractalkine-CX3CR1 cell infiltration system in inflammatory diseases on the basis of the analyses using CX3CR1 knockout mice (arteriosclerosis [Non-patent document 8], tissue damage caused by ischemic reperfusion [Non-patent document 9]), analyses of pathological animal models of inflammatory diseases using anti-fractalkine monoclonal antibodies (mouse type II collagen-induced arthritis, experimental autoimmune encephalomeningitis (Patent document 1), concanavalin A-induced hepatopathy (Patent document 1), analyses of pathological animal models using anti-CX3CR1 antiserum (WKY rat crescentic nephritis [Non-patent document 10], cardiac allograft rejection [Non-patent document 11]), or analyses of pathological animal models of inflammatory diseases using a fractalkine-inhibited mutant (MRL/lpr lupus nephritis [April 2004, Japan College of Rheumatology]), and thus construction of a novel treatment system for inflammatory diseases is expected. However, details of the mechanism of these actions for improving pathological conditions exhibited by the inhibition of the fractalkine-CX3CR1 interaction remain unknown under the present circumstances.

As for the classification of leukocytes, lymphocytes, monocytes and granulocytes have each been classified into small groups on the basis of many cell surface markers so far. Recently, they have been further classified into smaller groups according to the distribution of chemokine receptors, and a group that used to be regarded as one single group is being found to be a collection of several subgroups. It has been reported from analyses of mice that CX3CR1 is expressed in monocytes, NK cells and a part of T cells as described above, and it is being elucidated that there are two groups of monocytes among those, a group of those strongly expressing CX3CR1, but not expressing CCR2 ($CX3CR1^{high}CCR2-$) and a group of those weakly expressing CX3CR1 and strongly expressing CCR2 ($CX3CR1^{low}CCR2+$). Analyses of CX3CR1-knockout mice and CCR2-knockout mice have suggested that the $CX3CR1^{low}CCR2+$ monocytes are induced on inflammation sites upon inflammation and contribute to tissue damage by producing inflammatory cytokines such as TNFα and inducible nitrogen oxide synthetase (iNOS) as a potent nitrogen oxide (NO) synthetase (Non-patent documents 12 and 13). However, functions and significance of the $CX3CR1^{high}CCR2-$ monocytes upon inflammation have not been mentioned, and it is rather said that they are necessary for constitutive supply of tissue macrophages when there is no inflammation, and it is undesirable to inhibit functions of these cells.

Further, monocytes in human peripheral blood are also precisely classified on the basis of cell surface markers (CD16, CD62L etc.) and expression of CX3CR1. It is reported that one of the groups, CD16+CD62L- monocytes, increase in peripheral blood in inflammatory diseases, and the involvement thereof in progression of pathological conditions is strongly suggested. Since it has been reported the CD16+CD62L- monocytes highly express CX3CR1, it is anticipated that the CD16+CD62L- monocytes have properties substantially similar to those of the aforementioned mouse $CX3CR1^{high}CCR2-$ monocytes (Non-patent document 14). Further, since it has already been reported that the CD16+CD62L- monocytes strongly produce TNFα and iNOS, they are considered to strongly associate with progression of pathological conditions, along with their increase in peripheral blood in inflammatory diseases. However, there has been no specific report about whether production of TNFα and iNOS by these cells is inhibited by inhibition of the functions of CX3CR1.

iNOS, which has the highest NO synthesizing ability, is not constantly expressed unlike endothelial NOS (eNOS) and neural NOS (nNOS), and it is induced by stimulatory factors (for example, inflammatory cytokines and/or lipopolysaccharides etc.), transiently produced in a large amount and involved in biophylactic reactions such as elimination of bacteria, viruses, fungi or parasites. However, since excessive NO production leads to tissue damage, it is considered that excessive iNOS production in lesions may be a major factor for progressing pathological conditions. Examples of diseases in which NO is actually involved in development or progression of pathological conditions include inflammatory diseases (for example, rheumatic inflammation, rheumatoid arthritis, osteoarthritis, Crohn's disease, ulcerative colitis, psoriasis, arteriosclerosis, autoimmune diseases, acute inflammation etc.), allergy diseases (asthma, atopic dermatitis), ischemic diseases (for example, various cardiac disorders and cerebral disorders caused by infarct or ischemia, reperfusion disorder after ischemia etc.), shock (for example, endotoxic shock, hemorrhagic shock, cardiogenic shock etc.), pathological hypotension (for example, hypotension in cancer treatments using cytokines, hypotension caused by sepsis, hemorrhagic shock or cirrhosis etc.), transplant rejection, nervous system disorders (for example, Alzheimer's disease, epilepsy, migraine etc.), tumors, insulin-dependent diabetes, and so forth.

Furthermore, on the basis of analyses of inhibition of the iNOS activity in pathological models or iNOS-knockout mice, there have been reported improvement of pathological conditions in rheumatoid arthritis (Non-patent document 15), osteoarthritis (Non-patent document 16), inflammatory bowel diseases of which typical examples are ulcerative colitis and Crohn's disease (Non-patent documents 17 and 18), concanavalin A-induced hepatopathy (Non-patent document 19), asthma (Non-patent document 20), endotoxin-induced acute lung injury (Non-patent document 21), arteriosclerosis (Non-patent document 22), ischemic diseases (Non-patent documents 23, 24 and 25), transplant rejection (Non-patent document 22), and so forth.

In fact, improvement of pathological conditions by inhibition of the iNOS activity in many pathological model animals or in iNOS-knockout mice has been reported as described above. However, no promising drug that inhibits the iNOS activity has been launched.

Further, while inhibition of excessive NO production by inhibitors of enzymatic activity of iNOS improves hypotension commonly observed in septic shock, tissue destruction such as that in vasoparalysis and organ disorders, a risk of blocking the fundamental physiological functions of NO such as regulation of blood pressure and blood flow has been suggested (Non-patent document 26). In particular, in the analysis of cardiac muscle functions in sepsis using iNOS knockout mouse, differences in the role of iNOS depending on the type of cells producing it have been pointed out. iNOS expressed in cardiac muscle cells is essential to the useful reaction for shortening cardiac muscle cells by adrenergic stimulus in the event of sepsis, whereas iNOS expressed in inflammatory cells infiltrated in the vicinity of cardiac muscle cells is involved in a harmful reaction of damaging cardiac muscle cells (Non-patent document 27).

Therefore, it has been desired to provide a drug based on a novel approach, that is, inhibition of iNOS activity selective to cell species, for example, not general inhibition of the enzymatic reaction of iNOS, but inhibition of the enzymatic reaction of iNOS or inhibition of iNOS production in inflammatory cells.

Non-patent document 1: Arthritis Rheum., 2002 November, 46(11): 2878-83
Non-patent document 2: Am. J. Pathol., 2001 March, 158(3): 855-66
Non-patent document 3: J. Allergy Clin. Immunol., 2004 May, 113(5): 940-8
Non-patent document 4: J. Clin. Invest., 2001 May. 107(9): 1173-81
Non-patent document 5: J. Allergy Clin. Immunol., 2003 December, 112(6): 1139-46
Non-patent document 6: J. Clin. Invest. 2003 April, 111(8): 1241-50
Non-patent document 7: Clin. Exp. Immunol., 1999 November, 118 (2): 298-303
Non-patent document 8: Circulation, 2003 Feb. 25, 107(7): 1009-16
Non-patent document 9: J. Neuroimmunol., 2002 April, 125 (1-2): 59-65
Patent document 1: Japanese Patent Laid-open (Kokai) No. 2002-345454
Non-patent document 10: Kidney Int., 1999 August, 56(2): 612-20
Non-patent document 11: J. Clin. Invest., 2001 September, 108(5): 679-88
Non-patent document 12: Immunity, 2003 July, 19(1): 71-82
Non-patent document 13: Immunity, 2003 July, 19(1): 59-70
Non-patent document 14: J. Exp. Med., 2003 Jun. 16, 197 (12): 1701-7
Non-patent document 15: Eur. J. Pharmacol., 2002 Oct. 18, 453(1): 119-29
Non-patent document 16: Arthritis Rheum., 1998 July, 41(7): 1275-86
Non-patent document 17: J. Pharmacol. Exp. Ther., 2001 September, 298(3): 1128-32
Non-patent document 18: Eur. J. Pharmacol., 2001 Jan. 19, 412(1): 91-9
Non-patent document 19: J. Clin. Invest., 2001 February, 107(4): 439-47
Non-patent document 20: J. Pharmacol. Exp. Ther., 2003 March, 304(3): 1285-91
Non-patent document 21: Anesth. Analg., 2003 December, 97(6): 1751-5
Non-patent document 22: Eur. J. Pharmacol., 2000 Mar. 10, 391(1-2): 31-8
Non-patent document 23: Br. J. Pharmacol., 1999 May, 127 (2): 546-52
Non-patent document 24: Am. J. Physiol. Heart Circ. Physiol., 2002 June, 282(6): H1996-2003
Non-patent document 25: Nitric Oxide, 2004 May, 10(3): 170-7
Non-patent document 26: Curr. Drug Targets Inflamm. Allergy, 2002 March, 1(1): 89-108
Non-patent document 27: Circulation, 2003 Sep. 2, 108(9): 1107-12

DISCLOSURE OF THE INVENTION

An object of the present invention is to provide a therapeutic agent for inflammatory diseases, specifically, inflammatory bowel diseases (in particular, ulcerative colitis, Crohn's disease), psoriasis, atopic dermatitis, asthma, arteriosclerosis, tissue damage caused by ischemic reperfusion, acute respiratory distress syndrome, and so forth, based on a novel concept.

On the basis of the previous findings, the inventors of the present invention paid attention to the fact that there had been no report on inhibition of iNOS production and improvement of pathological conditions thereby by inhibition of the function of CX3CR1, thus constructed a hypothesis that a therapeutic agent for an inflammatory disease based on a novel concept could be created by elucidation of the function, and conducted various researches.

That is, investigation was performed by using antibodies inhibiting the interaction of fractalkine and CX3CR1 and the function of CX3CR1 in various animal models described in the examples mentioned later, and as a result, it was found for the first time that they inhibited iNOS production and improved pathological conditions. Further, although it had been reported that the antibodies inhibiting the interaction of fractalkine and CX3CR1 and the function of CX3CR1 are effective for ConA-induced hepatitis, it was found for the first time that they inhibited expression of iNOS mRNA in the liver in ConA-induced hepatitis and iNOS production in inflammatory cells. On the basis of these findings, they showed that an antibody inhibiting the interaction of fractalkine and CX3CR1 and the function of CX3CR1 or a compound inhibiting the interaction of fractalkine and CX3CR1 and the function of CX3CR1 (henceforth also referred to as "CX3CR1 antagonist") was useful for the treatment of inflammatory diseases associated with the fractalkine-CX3CR1 cell infiltration system and caused by excessive NO production by the iNOS activity or inflammatory cells (inflammatory bowel diseases [in particular, ulcerative colitis and Crohn's disease], psoriasis, atopic dermatitis, asthma, arteriosclerosis, tissue damage caused by ischemic reperfusion, acute respiratory distress syndrome etc.), and thus accomplished the present invention.

That is, the present invention provides the followings.
(1) A therapeutic agent for an inflammatory disease comprising an antibody or a CX3CR1 antagonist, wherein said antibody or said CX3CR1 antagonist inhibits an interaction of fractalkine and CX3CR1.
(2) The agent according to (1), wherein the antibody is an anti-fractalkine antibody.
(3) The agent according to (2), wherein the anti-fractalkine antibody is a monoclonal antibody.
(4) The agent according to (3), wherein the anti-fractalkine antibody is a monoclonal antibody 5H8-4 produced by a hybridoma of the accession No. FERM BP-10372 or a monoclonal antibody #126 produced by a hybridoma of the accession No. FERM BP-10371.
(5) The agent according to any one of (1) to (4), wherein the inflammatory disease is an inflammatory bowel disease.
(6) The agent according to (5), wherein the inflammatory disease is ulcerative colitis or Crohn's disease.
(7) The agent according to any one of (1) to (4), wherein the inflammatory disease is psoriasis.
(8) The agent according to any one of (1) to (4), wherein the inflammatory disease is atopic dermatitis.
(9) The agent according to any one of (1) to (4), wherein the inflammatory disease is asthma.
(10) The agent according to any one of (1) to (4), wherein the inflammatory disease is arteriosclerosis.
(11) The agent according to any one of (1) to (4), wherein the inflammatory disease is tissue damage caused by ischemic reperfusion.
(12) The agent according to any one of (1) to (4), wherein the inflammatory disease is acute respiratory distress syndrome.
(13) A hybridoma Ham @mFKN#126.1.1 of the accession No. FERM BP-10371.
(14) A monoclonal antibody #126 produced by the hybridoma according to (13).

Further, there are also provided a method for treating an inflammatory disease, which comprises the step of administering a therapeutically effective amount of an antibody or a CX3CR1 antagonist that inhibits an interaction of fractalkine and CX3CR1 to a patient who needs treatment of an inflammatory disease, and use of an antibody or a CX3CR1 antagonist that inhibits an interaction of fractalkine and CX3CR1 in the production of a therapeutic agent for an inflammatory disease.

BEST MODE FOR CARRYING OUT THE INVENTION

<1> Deposition of Microorganisms

Figure 1:
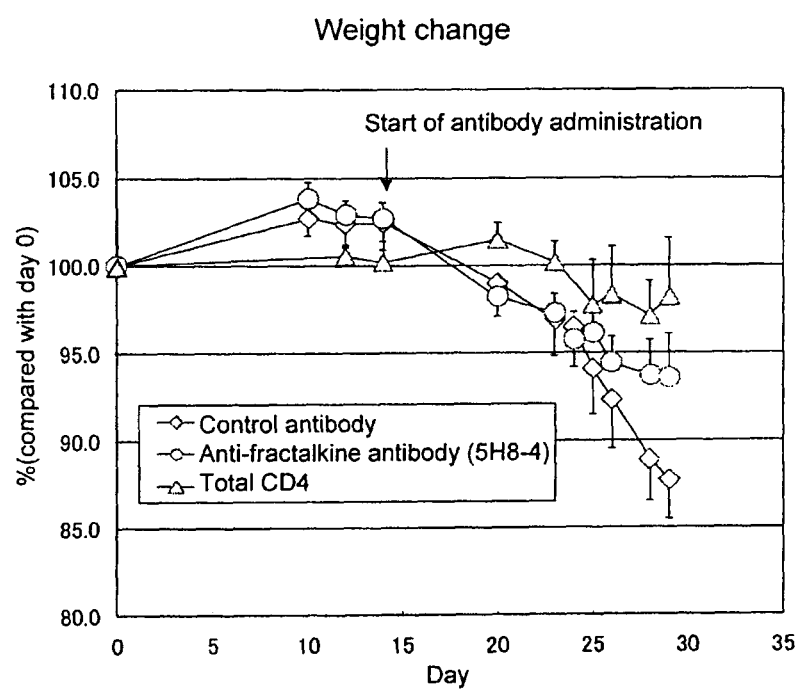
FIG. 1 It shows effect of the anti-mouse fractalkine antibody (5H8-4) for improving body weight loss in a mouse inflammatory bowel disease model transfused with CD4-positive and CD45RB strongly-positive T lymphocytes.

The hybridoma Ham @mFKN5H8-4 was deposited at International Patent Organism Depositary, National Institute of Advanced Industrial Science and Technology (Tsukuba Central 6, 1-1, Higashi 1-Chome, Tsukuba-shi, Ibaraki-ken, 305-8566, Japan) on Sep. 29, 2004 (Accession No.: FERM P-20236), and then the deposition was converted to an international deposition under the provisions of the Budapest Treaty (Accession No.: FERM BP-10372).

The hybridoma Ham @mFKN#126.1.1 was deposited at International Patent Organism Depositary, National Institute of Advanced Industrial Science and Technology (Tsukuba Central 6, 1-1, Higashi 1-Chome, Tsukuba-shi, Ibaraki-ken, 305-8566, Japan) on Sep. 29, 2004 (Accession No.: FERM P-20235), and then the deposition was converted to an international deposition under the provisions of the Budapest Treaty (Accession No.: FERM BP-10371).

<2> Antibody Inhibiting Interaction of Fractalkine and CX3CR1

Antibodies inhibiting the interaction of fractalkine and CX3CR1 can be prepared as follows.

A mammal (for example, mouse, hamster or rabbit) can be immunized with CX3CR1 or fractalkine in the form of an immunogen causing immune responses in the mammal or a protein fragment thereof (for example, peptide fragment).

An expression vector incorporated with the gene of CX3CR1 or fractalkine (for example, see GenBank NM_001337 or NM_002996) is expressed in host cells, for example, bacterial, mammal or insect cells, and CX3CR1 or fractalkine can be purified from a culture medium or bacterial cells or other cells according to a standard method. Further, CX3CR1 or fractalkine can be expressed as a fusion protein with, for example, GST or the like, and may be purified by using a glutathione column in the case of a fusion protein with GST.

A peptide of CX3CR1 or fractalkine can also be synthesized on the basis of the amino acid sequence of CX3CR1 or fractalkine by a known method (for example, F-moc or T-boc chemical synthesis), and immunogenicity of the synthesized peptide can be enhanced by binding it to a suitable carrier, for example, KLH.

After immunization with the purified CX3CR1 or fractalkine or a peptide fragment thereof and an adjuvant, an antiserum can be obtained, and polyclonal antibodies can be isolated from the antiserum if desired. Further, in order to produce monoclonal antibodies, antibody producing cells (lymphocytes) are collected from an immunized animal and fused with myeloma cells by a standard cell fusion method to immortalize the cells and thereby obtain hybridoma cells. This technique is an established method in this technical field, and can be implemented according to a suitable manual (Harlow et al., Antibodies: A Laboratory Manual, 1998, Cold Spring Harbor Laboratory). Further, monoclonal antibodies may be prepared by other methods such as the human B cell hybridoma method for producing human monoclonal antibodies (Kozbar et al., Immunol. Today, 4: 72, 1983), EBV-hybridoma method (Cole et al., Monoclonal Antibody in Cancer Therapy, 1985, Allen R. Bliss, Inc., 77-96), and screening of a combinatorial antibody library (Huse et al., Science, 246: 1275, 1989).

Further, as an alternative method, also acceptable is a method in which a mammal is immunized with insect cells per se in which CX3CR1 is expressed, hybridomas are prepared from lymphocytes of the mammal, and screening of the produced antibodies is performed by using mammal cells in which CX3CR1 is expressed (cells showing low cross immunity with the insect cells and not bound with antibodies directed to proteins derived from the insect cells). Further, they can also be prepared by the method described in Japanese Patent Laid-open No. 2002-345454.

Screening for antibodies that inhibit the interaction of fractalkine and CX3CR1 can be performed by the screening method described later.

<3> CX3CR1 Antagonist

The present invention was accomplished on the basis of the finding that antibodies inhibiting the interaction of fractalkine and CX3CR1 are useful for treatment of inflammatory diseases associated with the fractalkine-CX3CR1 cell infiltration system and caused by excessive NO production by the iNOS activity or inflammatory cells. Therefore, compounds inhibiting the interaction of fractalkine and CX3CR1 and the function of CX3CR1, the CX3CR1 antagonists, can also be used in the present invention. The CX3CR1 antagonists are not particularly limited so long as compounds having the aforementioned action are used, and they may be known or novel compounds. Further, they may be compounds obtained by the screening method described later.

In the present specification, the "compounds" include expression products of a gene library, synthetic low molecular compound library, nucleic acids (oligo DNA, oligo RNA), synthetic peptide library, substances released from bacteria, cell (microorganisms, plant cells, animal cells) extracts, cell (microorganisms, plant cells, animal cells) culture supernatant, purified or partially purified polypeptides, extracts derived from marine organisms, plants, animals and so forth, soil and random phage peptide display library. Specific examples include the compounds described in International Patent Publications WO03/018549, WO00/09511 and WO02/076990, and so forth. Known compounds can be produced by a production method known per se, or when they are natural compounds, they can be obtained by an extraction method known per se or a purification method known per se, or when they are commercially available, they can be purchased. Further, derivatives of known compounds can be obtained by modification by chemical, physical and/or biochemical means.

<4> Screening Method for Antibodies Inhibiting Interaction of Fractalkine and CX3CR1

Antibodies or CX3CR1 antagonists inhibiting the interaction of fractalkine and CX3CR1 can be screened for on the bases of whether CX3CR1-positive cells migrate to cells expressing fractalkine or membrane-bound fractalkine. A specific method for screening on the basis of whether CX3CR1-positive cells migrate is described below. However, the present invention is not limited to this method.

Migration to fractalkine can be measured by using, for example, a transwell culture insert (Coaster).

Cells not expressing fractalkine, for example, ECV304 cells, are cultured on a transwell culture insert to form a single cell layer on the surface of the culture insert. Fractalkine is diluted with a migration solution (for example, RPMI-1640: M199=1:1, 0.5% BSA, 20 mM HEPES, pH 7.4) to an appropriate concentration, preferably a concentration of 10 nM, and added to a 24-well plate. The transwell culture insert on which ECV304 cells are cultured is attached to the 24-transwell, and an appropriate number, preferably $10^6$, of peripheral blood monocytes suspended in the migration solution are added to the transwell culture insert. The cells are cultured under an appropriate condition, preferably, at 37° C. for 4 hours, then cells that migrate to the well plate through the ECV304 cells are collected and identified on the basis of cell surface markers or intracellular antigens. Preferably, they are stained with fluorescence by using antibodies labeled with fluorescence directed to a cell surface marker or intracellular antigen, and then quantified by using the FACS calibur.

If migration of killer lymphocytes, preferably cells expressing perforin and granzyme B or CX3CR1, more preferably cells expressing CX3CR1, is inhibited when antibodies that bind to CX3CR1 or fractalkine is added to the migration solution, the antibodies are determined to inhibit the interaction of fractalkine and CX3CR1.

Further, by expressing membrane-bound fractalkine in ECV304 cells and measuring peripheral blood monocytes that migrate to other chemokines such as MIP-1β, whether an antibody inhibits the interaction of fractalkine and CX3CR1 can also be determined.

<5> Inhibition of iNOS Production

In the present specification, the expression "inhibition of iNOS production" or "iNOS production is inhibited" means that the expression level of mRNA for iNOS is suppressed, or the production amount of iNOS protein is suppressed. Inhibition of iNOS production can be measured by any of real time PCR, Western blotting, ELISA (solid phase enzyme-linked immunosorbent assay) and iNOS enzyme activity measurement. For example, the real time PCR is specifically performed as follows. Total RNA is purified from tissues or cells in a conventional manner, and cDNA is prepared by using a reverse transcriptase and suitable primers. From the prepared cDNA, each molecule can be specifically amplified by using primers specific to each molecule and a DNA polymerase. An amplification curve for each molecule can be monitored by incorporating an a suitable fluorescent dye into the molecule when it is amplified and using a specific apparatus (PRISM 7700 Sequence Detector (Applied Biosystems) etc.). The mRNA expression level of each molecule in tissues and cells can be quantitatively measured by correcting each molecule using an internal standard gene (glyceraldehyde-3-phosphate dehydrogenase gene etc.).

<6> Use of Antibody or CX3CR1 Antagonist Inhibiting Interaction of Fractalkine and CX3CR1

The present invention provides a therapeutic agent for an inflammatory disease containing an antibody or a CX3CR1 antagonist inhibiting the interaction of fractalkine and CX3CR1. In the aforementioned therapeutic agent, the aforementioned antibody preferably an antibody that binds to fractalkine. When the therapeutic agent of the present invention containing the antibody is applied to humans, the following embodiments are preferred.

A monoclonal antibody prepared by using an animal other than human, for example, a mouse monoclonal antibody prepared by using mouse as an animal to be immunized, is often recognized as a foreign protein and often causes an immune response against a monoclonal antibody, when it is administered to a human. One means for avoiding this problem is a chimeric antibody, that is, an antibody consisting of an antigen binding region derived from a mouse monoclonal antibody and the other regions derived from a human antibody. The antibodies inhibiting the interaction of fractalkine and CX3CR1 used in the present invention also include chimeric antibodies. Examples of chimeric antibodies include a chimeric antibody using the entire variable region of a mouse monoclonal antibody as the antigen binding region (Morrison et al., Proc. Natl. Acad. Sci. USA, 81: 6851, 1985; Takeda et al., Nature, 314: 452, 1985) and a chimeric antibody using a human-derived framework region and a hypervariable region derived from a mouse monoclonal antibody in combination as the antigen binding region (Teng et al., Proc. Natl. Acad. Sci. USA, 80: 7308-12, 1983; Kozbar et al., Immunol. Today, 4: 7279, 1983). However, the present invention is not limited to these examples.

Further, the antibodies inhibiting the interaction of fractalkine and CX3CR1 referred to in the present specification also include a fragment of an antibody specifically binding to CX3CR1 or fractalkine, for example, Fab or (Fab')$_2$ fragment.

The therapeutic agent of the present invention can be administered to patients who need treatment of inflammatory diseases associated with the fractalkine-CX3CR1 cell infiltration system and caused by excessive NO production by the iNOS activity or inflammatory cells, specifically, inflammatory bowel diseases (in particular, ulcerative colitis, Crohn's disease), psoriasis, atopic dermatitis, asthma, arteriosclerosis, tissue damage caused by ischemic reperfusion, acute respiratory distress syndrome, and so forth. The inflammatory diseases may be autoimmune diseases or other inflammatory diseases. Further, the inflammatory diseases may be nephritis, myocarditis, autoimmune hepatopathy, multiple sclerosis, rheumatism or other inflammatory diseases.

The therapeutic agent of the present invention can be administered in a conventional manner such as injection (subcutaneous, intravenous injections etc.).

The form of the therapeutic agent is suitably selected depending on the administration method and may be a pharmaceutical composition using pharmaceutically acceptable carriers in combination. Examples of the pharmaceutical composition suitable for injection include sterilized aqueous solution (when the ingredients are water-soluble), dispersion, or and sterilized powder used to immediately prepare sterilized injection solution or dispersion. All the pharmaceutical compositions suitable for injection must be sterilized and have fluidity enabling easy injection operation. These compositions must be stable under production and storage conditions and must be protected from actions of contaminating microorganisms such as bacteria and fungi. Examples of the carriers include water, ethanol, polyols (for example, glycerol, propylene glycol, polyethylene glycol etc.), solvents or dispersion media comprising an appropriate mixture of these. Suitable fluidity can be maintained by, for example, using a coating of lecithin or the like to maintain a required grain size in the case of dispersions or using a surfactant. Protection from actions of microorganisms can be implemented by using various antibacterial agents and antifungal agents such as paraben, chlorobutanol, phenol, ascorbic acid and thimerosal. In many cases, the composition preferably contains an isotonic agent, for example, sugars, polyalcohols such as mannitol and sorbitol, sodium chloride, and so forth. Sustained absorption of the composition for injection can be achieved by mixing an agent delaying absorption such as aluminum monostearate and gelatin in the composition.

A solution for injection can be prepared by mixing a required amount of the antibody inhibiting the interaction of fractalkine and CX3CR1 and one or a mixture of the aforementioned components in a suitable solvent if necessary and then subjecting the mixture to sterilization filtration. In general, a dispersion is prepared by mixing an active compound in a sterilized medium containing a basic dispersion medium and other required components selected from those mentioned above. Preferred methods for preparing sterilized powder used for preparation of a sterilized injection solution are vacuum drying and lyophilization, and powders containing the active ingredient and desired additional components subjected to sterilization filtration beforehand can be obtained by these methods.

Dose of the therapeutic agent of the present invention may vary depending on the selected antibody, object of administration, age, sex and susceptibility to drugs of patient, administration method, history of the disease and so forth, and may be changed by physician's discretion. However, the suitable dose range is, for example, about 0.01 to 30 mg, preferably about 0.1 to 10 mg, per kg of body weight of the patient. Taking into account that efficiency of the administration routes varies, the required dose is expected to change in a wide range. For example, it is expected that oral administration requires a dose higher than that for administration by intravenous injection. Such changes in the dose level can be adjusted by using a standard empirical optimization procedure well understood in this field.

Further, an immunotoxin containing an antibody directed to CX3CR1 and a cytotoxic substance bound to the antibody may be prepared.

Examples of the toxic substance include saporin, ricin, Pseudomonas exotoxin, diphtheria toxin, chemotherapeutic agents and so forth. The antibody and the toxic substance can be bound by a conventional method used for preparation of immunotoxins. Such an immunotoxin specifically inhibits growth of CX3CR1 expressing cells.

When a therapeutic agent for inflammatory diseases containing the CX3CR1 antagonist is applied to humans, the following embodiments are preferred. The CX3CR1 antagonist may form a salt, and examples thereof include salts with pharmaceutically acceptable acids or bases and so forth. Accordingly, the CX3CR1 antagonist or a salt thereof can be used for treatment of inflammatory diseases associated with the fractalkine-CX3CR1 cell infiltration system and caused by excessive NO production by the iNOS activity or inflammatory cells, specifically, inflammatory bowel diseases (in particular, ulcerative colitis and Crohn's disease), psoriasis, atopic dermatitis, asthma, arteriosclerosis, tissue damage caused by ischemic reperfusion, acute respiratory distress syndrome, and so forth. The obtained substances per se can be solely used, or they can also be used as a pharmaceutical composition by mixing them with a pharmaceutically acceptable carrier. The proportion of the active ingredient to the carrier in such a case can be changed in the range of 1 to 90% by weight. Further, the therapeutic agent can be administered via any of oral or parenteral administration routes (for example, intravenous injection, intramuscular injection, subcutaneous administration, rectal administration or percutaneous administration).

Therefore, a pharmaceutical composition containing the CX3CR1 antagonist or a salt thereof is prepared in a suitable dosage form depending on the administration route, and specific examples of the dosage form include oral agents such as tablet, capsule, granule, powder and syrup, and parenteral agents such as injection, drip infusion, liposome and suppository. These preparations can be produced in a conventional manner using usually used excipients, extenders, binders, wetting agents, disintegrating agents, surfactants, lubricants, dispersing agents, buffers, preservatives, dissolving aids, antiseptics, flavoring agents, soothing agents, stabilizers, and so forth. Examples of usable nontoxic additives mentioned above include lactose, fructose, glucose, starch, gelatin, magnesium stearate, methylcellulose or salts thereof, ethanol, citric acid, sodium chloride, sodium phosphate and so forth.

Administration form and required dose range thereof depend on selection of the obtained compounds, object of administration, administration route, property of the preparation and conditions of patient as well as physician's discretion. However, the suitable dose range is about 1.0 to 1,500 µg, preferably about 10 to 500 µg, per kg of body weight of the patient. Taking into account that efficiency of the administration route varies, the required dose is expected to be changed in a wide range. For example, it is expected that oral administration requires a dose higher than that for administration by intravenous injection. Such changes in the dose level can be adjusted by using a standard empirical optimization procedure well understood in this field.

In the present specification, "treatment" generally means to obtain a desired pharmacological effect and/or physiological effect. The effect may be prophylactic in view of completely or partially preventing a disease and/or a symptom, or may be therapeutic in view of partially or completely curing a disease and/or adverse effect of the disease. In the present specification, "treatment" includes arbitrary treatments of diseases in mammals, in particular, humans, for example, the following treatments (a) to (c):
(a) Prevention of onset of a disease or symptom in a patient who may have a predisposition of the disease or symptom, but is not yet diagnosed to have the predisposition;
(b) Inhibition of a symptom of a disease, that is, prevention of progression of the symptom;
(c) Amelioration of a symptom of a disease, that is, induction of regression of the disease or symptom.

Since the antibody or the CX3CR1 antagonist inhibiting the interaction of fractalkine and CX3CR1 used in the present invention has an action of inhibiting iNOS production, an iNOS production inhibitor containing the CX3CR1 antagonist as an active ingredient is also provided. The iNOS production inhibitor may be prepared as a composition like the aforementioned therapeutic agent, and can be administered to a patient who needs inhibition of iNOS production in the same manner as that for the aforementioned therapeutic agent.

Hereafter, the present invention will be explained in more detail with reference to examples. However, these are mentioned as embodiments, and the scope of the present invention is not limited at all by these examples. The abbreviations used in the following description are according to those conventionally used in this field.

Example 1

Effect of Anti-Fractalkine Antibody (5H8-4) in Mouse Inflammatory Bowel Disease Model Transfused with CD4-Positive and CD45RB Strongly-Positive (CD4+CD45RB$^{high}$) T Lymphocytes (1) Preparation of Anti-Fractalkine Antibody (5H8-4)

The anti-fractalkine antibody (5H8-4) was prepared by the following method (Japanese Patent Laid-open No. 2002-345454). Mouse fractalkine (R&D) was used as an antigen. The antigen was mixed with TiterMax adjuvant, Armenian hamsters were immunized with the mixture, and booster immunizations were performed thereafter with the antigen alone. The antibody titer in the serum was measured by ELISA. Lymphocytes were isolated from the Armenian hamsters in which the antibody titer increased, the lymphocytes and P3 myeloma cells were mixed at a ratio of 5:1, and the cells were fused by using PEG (Boehringer). The hybridomas were cultured on a 96-well plate for one week by using RPMI-1640/10% FCS/HAT/10% Origen HCF (ISGN). Then, ELISA was performed for the culture supernatant to identify positive wells. The hybridomas producing anti-mouse fractalkine antibodies were subjected to limiting dilution twice for cloning. The monoclonal antibodies were purified by using a protein A column from the ascites prepared by inoculating the hybridomas to SCID mice to which the incomplete Freund's adjuvant was administered. The neutralization activity was determined by using inhibition of migration of CX3CR1 expressing cells to mouse fractalkine as an index to obtain a neutralizing antibody (5H8-4). The hybridoma producing the neutralizing antibody was designated as Ham @mFKN5H8-4.

(2) Method

As for preparation of an inflammatory bowel disease model transfused with CD4-positive and CD45RB strongly-positive (CD4+CD45RB$^{high}$) T lymphocytes, reference was made to Powrie et al., Int. Immunol., 5, 1461-1471, 1993. The spleens were removed from 8- to 10-week old female Balb/c mice (Charles River Laboratories Japan, Inc.), and the tissues were ground on a cell strainer (PharMingen) having a pore diameter of 100 μm to separate spleen cells. The separated spleen cells, 5 ml of ammonium chloride solution (0.75% ammonium chloride, 16 mM Tris buffer, pH 7.4) was added per each spleen and the mixture was left at room temperature for 15 minutes to lyse erythrocytes. To the spleen cell solution, PBS was added in a volume of 2 times and the mixture was centrifuged at 1500 rpm for 5 minutes, to collect the precipitates. CD4 T lymphocytes were purified from the separated spleen cells by using CD4 T Cell Isolation Kit (Milteny). To separate CD4-positive and CD45RB strongly-positive T lymphocytes, the purified CD4 T lymphocytes were subjected to double staining using phycoerythrin (PE)-labeled anti-CD4 antibody (eBioscience) and fluorescein isothiocyanate (FITC)-labeled anti-CD45RB antibody (eBioscience). After the double staining, CD4-positive and CD45RB strongly-positive cells were sorted by using FACSAria (Becton-Dickinson) to collect the objective cells. The collected cells were washed with PBS and then suspended in PBS at a cell density of $2\times10^6$ cells/ml. The CD4-positive and CD45RB strongly-positive cells prepared above were transfused into the peritoneal cavities of 8- to 10-week old female SCID mice (Clea Japan, Inc.) in a volume of 200 μl each, that is, $4\times10^5$ cells/mouse. Seven SCID mice in each group transfused with the CD4-positive and CD45RB strongly-positive cells were given with 500 μg of a control antibody (hamster IgG) or 500 μg of the anti-fractalkine antibody (5H8-4) (antibody in PBS) once every three days from two weeks after the cell transfusion. The administration was performed from the caudal vein. Further, as a negative control group, four SCID mice transfused with mouse CD4 T lymphocytes (total CD4) that were purified by using CD4 T cell Isolation Kit (Milteny) and not separated on the basis of the expression level of CD45RB in an amount of $1.2\times10^6$ cells/mouse were used. Two weeks after the administration of each antibody, autopsy was performed, and evaluation was performed on the basis of body weight loss, scores of stool consistency in the large intestine, development of large intestine hypertrophy, iNOS mRNA expression analysis and pathological observation. As the stool consistency scores, the stool consistency scores used for analysis of dextran sulfate sodium-induced colitis (Cooper et al., Lab. Invest., 69, 238-249, 1993) shown in Table 1 were used.

TABLE 1

| Stool consistency scores | |
| --- | --- |
| Stool consistency | |
| Score 0 | Normal |
| Score 1 | Loose stool (shape is substantially normal) |
| Score 2 | Loose stool (shape is maintained) |
| Score 3 | Loose stool (shape is abnormal) |
| Score 4 | Diarrhea, stool attaches around anus |

Further, for large intestine hypertrophy, a site about 1.5 cm from the anal region was measured by using Dial Thickness Gauge (Peacock) after removing intestinal contents. Further, the large intestine was subjected to morphological observation and histopathological observation based on Mayer's hematoxylin eosin staining of tissue sections.

Further, expressions of mRNAs for iNOS and so forth were analyzed by real time PCR using, as a template, cDNA obtained by purifying total RNA (500 ng) from the large intestine using RNeasy Mini Kit (QIAGEN) and reverse transcribing it using AMV reverse transcriptase (TAKARA) and a random hexamer (TAKARA). The real time PCR was performed for a reaction mixture prepared by mixing various primers with reagents of QuantiTect SYBR Green PCR Kit (Qiagen) and uracil-DNA-glycosylase (Invitrogen) by using ABI PRISM 7700 Sequence Detector (Applied Biosystems). PCR was performed by reactions at 50° C. for 2 minutes and at 95° C. for 15 minutes and 35 cycles of reactions at 95° C. for 15 seconds and at 60° C. for 1 minute. The used primer sets are as follows.

TABLE 2

| Primer | Sequence | SEQ ID NO: |
|---|---|---|
| miNOS sense | 5'-AGCTGAACTTGAGCGAGGAG-3' | 1 |
| miNOS anti-sense | 5'-TGCCCCATAGGAAAAGACTG-3' | 2 |
| mfractalkine (FKN) sense | 5'-GGCAAGATGACCTCACGAAT-3' | 3 |
| mfractalkine (FKN) anti-sense | 5'-CTGTGTCGTCTCCAGGACAA-3' | 4 |
| mIFN-γ sense | 5'-GCTTTAACAGCAGGCCAGAC-3' | 5 |
| mIFN-γ anti-sense | 5'-GGAAGCACCAGGTGTCAAGT-3' | 6 |
| mTNF α sense | 5'-CCAGTGTGGGAAGCTGTCTT-3' | 7 |
| mTNF α anti-sense | 5'-AAGCAAAAGAGGAGGCAACA-3' | 8 |
| mIL-4 sense | 5'-GGCATTTTGAACGAGGTCAC-3' | 9 |
| mIL-4 anti-sense | 5'-AAATATGCGAAGCACCTTGG-3' | 10 |
| mPerforin sense | 5'-TGCAAGCAGAAGCACAAGTT-3' | 11 |
| mPerforin anti-sense | 5'-TGTGTGTTCACTGGGAAGGA-3' | 12 |
| mGranzymeB (GrB) sense | 5'-CCATCGTCCCTAGAGCTGAG-3' | 13 |
| mGranzymeB (GrB) anti-sense | 5'-GCTGGTCCTTGTGAATGGAT-3' | 14 |
| mFasL sense | 5'-CTGTGGCTACCGGTGGTATT-3' | 15 |
| mFasL anti-sense | 5'-GTTCTGCCAGTTCCTTCTGC-3' | 16 |
| mFas sense | 5'-GGAGACAGGATGACCCTGAA-3' | 17 |
| mFas anti-sense | 5'-TTCAGCAATTCTCGGGATGT-3' | 18 |

(3) Results

Figure 2:
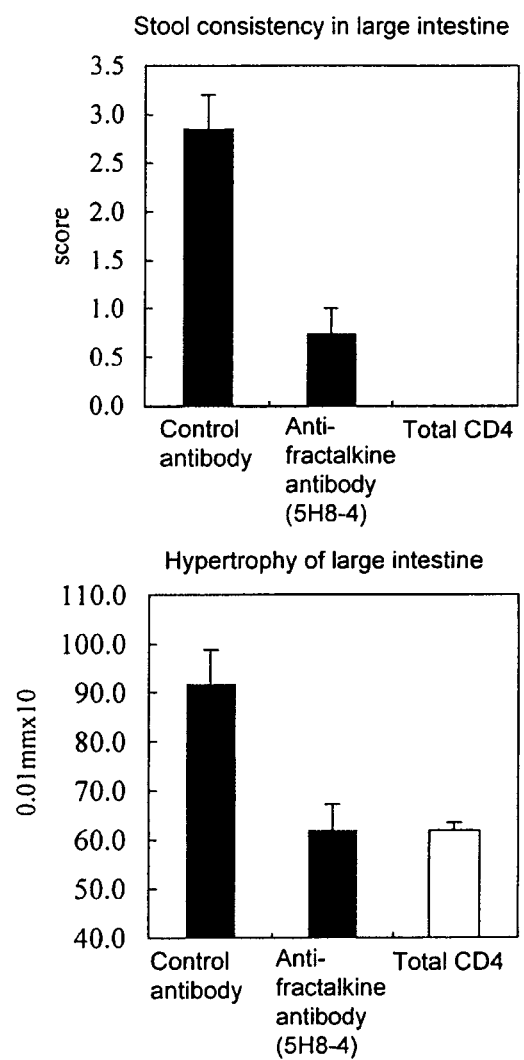
FIG. 2 It shows scores of stool consistency in the large intestine and effect of the anti-mouse fractalkine antibody (5H8-4) for improving hypertrophy of the large intestine in a mouse inflammatory bowel disease model transfused with CD4-positive and CD45RB strongly-positive T lymphocytes.
Figure 3:
FIG. 3 It shows effect of the anti-mouse fractalkine antibody (5H8-4) for improving morphological changes in the large intestine in a mouse inflammatory bowel disease model transfused with CD4-positive and CD45RB strongly-positive T lymphocytes (photographs of organ morphology).
Figure 3:
Figure 4:
FIG. 4 It shows effect of the anti-mouse fractalkine antibody (5H8-4) for improving large intestine tissue damage in a mouse inflammatory bowel disease model transfused with CD4-positive and CD45RB strongly-positive T lymphocytes (microphotographs).
Figure 4:
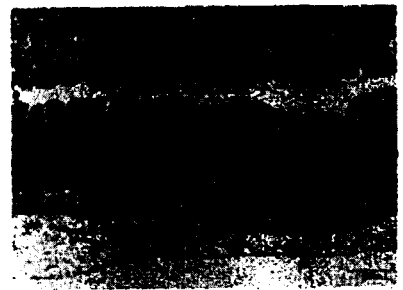
Figure 5:
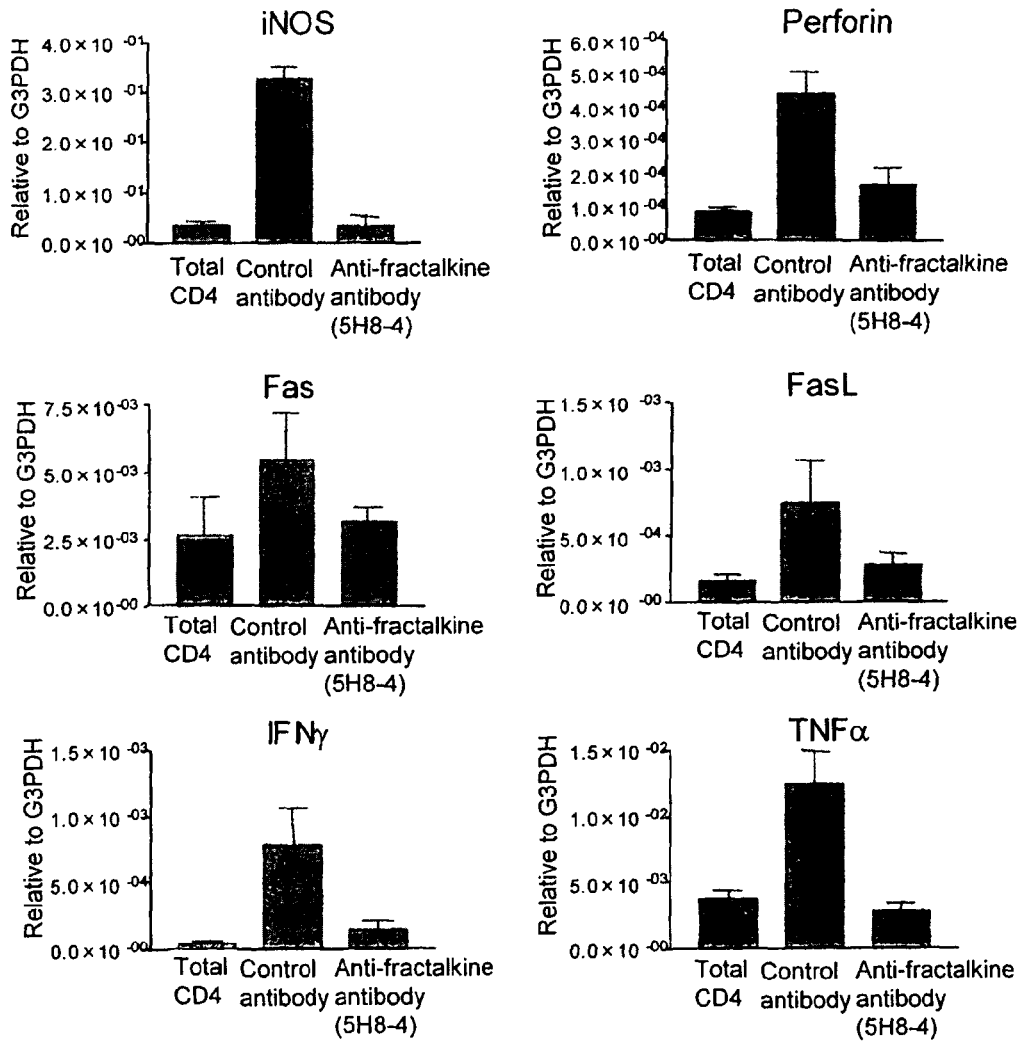
FIG. 5 It shows effect of the anti-mouse fractalkine antibody (5H8-4) for improving expressions of mRNAs for various factors in a mouse inflammatory bowel disease model transfused with CD4-positive and CD45RB strongly-positive T lymphocytes.

The body weight loss was suppressed in the anti-fractalkine antibody (5H8-4) administration group compared with the control antibody administration group (FIG. 1). Further, the consistency scores of stool in the large intestine and large intestine hypertrophy were improved in the anti-fractalkine antibody (5H8-4) administration group compared with the control antibody administration group (FIG. 2). As for the morphological observation of the large intestine sites, hypertrophy was observed at sites from the colon to the rectum in the control antibody administration group, and improvement was observed by administration of the anti-fractalkine antibodies (5H8-4) (FIG. 3). In tissue section staining, a very large number of leukocytes (T lymphocytes, monocytes, macrophages etc.) infiltrated into the large intestine mucosal layer, and disappearance of goblet cells producing mucus, and damage and hyperplasia of the large intestine epithelial tissues were observed in the control antibody group. In contrast, in the anti-fractalkine antibody (5H8-4) administration group, leukocyte infiltration was inhibited, and large intestine epithelial cells were hardly damaged (FIG. 4). Further, as for mRNA expression, expression of iNOS mRNA increased in the control antibody administration group, but the expression was markedly inhibited by the anti-fractalkine antibodies (5H8-4). Furthermore, expressions of mRNAs for cytotoxic factors such as perforin, Fas and FasL and cytokines such as IFNγ and TNFα also increased in the control antibody administration group. In contrast, inhibition of these expressions was observed in the anti-fractalkine antibody (5H8-4) administration group (FIG. 5). The above results revealed that the fractalkine-CX3CR1 pathway played an important role in the inflammatory bowel disease model transfused with CD4-positive and CD45RB strongly-positive (CD4+CD45RB$^{high}$) T lymphocytes. It was inferred that the action inhibited excessive NO production by inhibiting iNOS production and ameliorated tissue damages. That is, it was suggested that inhibition of iNOS production based on the inhibition of the interaction of fractalkine and CX3CR1 was a useful treatment system for inflammatory bowel diseases.

Example 2

Effect of Anti-Fractalkine Antibody (5H8-4) in Mouse Oxazolone-Induced Inflammatory Bowel Disease Model (1) Method As for the mouse oxazolone-induced inflammatory bowel disease model, reference was made to Iijima et al., J. Exp. Med., 199, 471-482, 2004. The abdomens of 8 to 10-week old male Balb/c mice (Charles River Laboratories Japan, Inc.) were shaved in an about 2-cm square. To each mouse, 150 μl each of 100% ethanol solution containing 3% 4-ethoxymethylene-2-phenyl-2-oxazolin-5-one (hereinafter referred to as oxazolone, Sigma) was applied. The animals were starved on the fourth day after the oxazolone sensitization, and on the fifth day, given an intestinal injection of 100 μl each of 50% ethanol/physiological saline containing 0.5% oxazolone at a site about 3 cm from the anus under diethyl ether anesthesia. As a negative control group, five normal Balb/c mice were given an intestinal injection of 100 μl each of 50% ethanol/physiological saline. To seven mice in each group given with the intestinal injection of oxazolone, 500 μg of a control antibody (hamster IgG) or 500 μg of the anti-fractalkine antibody (5H8-4) (antibody in PBS) was administered. The anti-fractalkine antibody (5H8-4) was administered on the fifth day after the sensitization (immediately before the intestinal injection of oxazolone). The antibody was administered from the caudal vein. The evaluation was performed for the evaluation items of Disease Activity Index (hereinafter referred to as DAI, stool consistency, blood content and body weight gain and loss were represented by scores, and DAI values were calculated), large intestine shortening, large intestine hypertrophy and pathological observation. As DAI, DAI used for evaluation of dextran sodium sulfate induced colitis (Cooper et al., Lab. Invest., 69, 238-249, 1993) shown in Table 3 was used.

TABLE 3

DAI

| | Body weight loss | Stool consistency | Bloody stool |
|---|---|---|---|
| Score 0 | 0% | Normal | Normal |
| Score 1 | 0-5% | Loose stool (shape is substantially normal) | Trace of blood in stool |
| Score 2 | 5-10% | Loose stool (shape is maintained) | Bloody stool (about half of stool) |
| Score 3 | 10-15% | Loose stool (shape is abnormal) | Bloody stool (most of stool) |
| Score 4 | >20% | Diarrhea, stool attaches around anus | Bleeding |

Further, since diarrhea and loose stool were observed from the second day after the intestinal injection of oxazolone, DAI was observed over time. The large intestine was subjected to morphological observation and histopathological observation based on Mayer's hematoxylin eosin staining of tissue sections.

(2) Results

Figure 6:
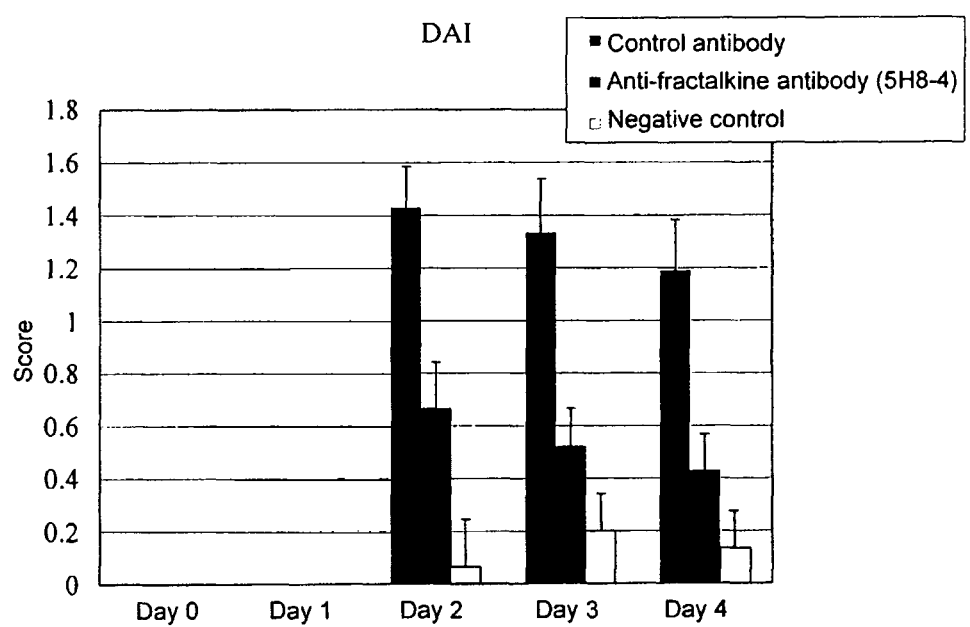
FIG. 6 It shows effect of the anti-mouse fractalkine antibody (5H8-4) for improving DAI in a mouse oxazolone-induced inflammatory bowel disease model.
Figure 7:
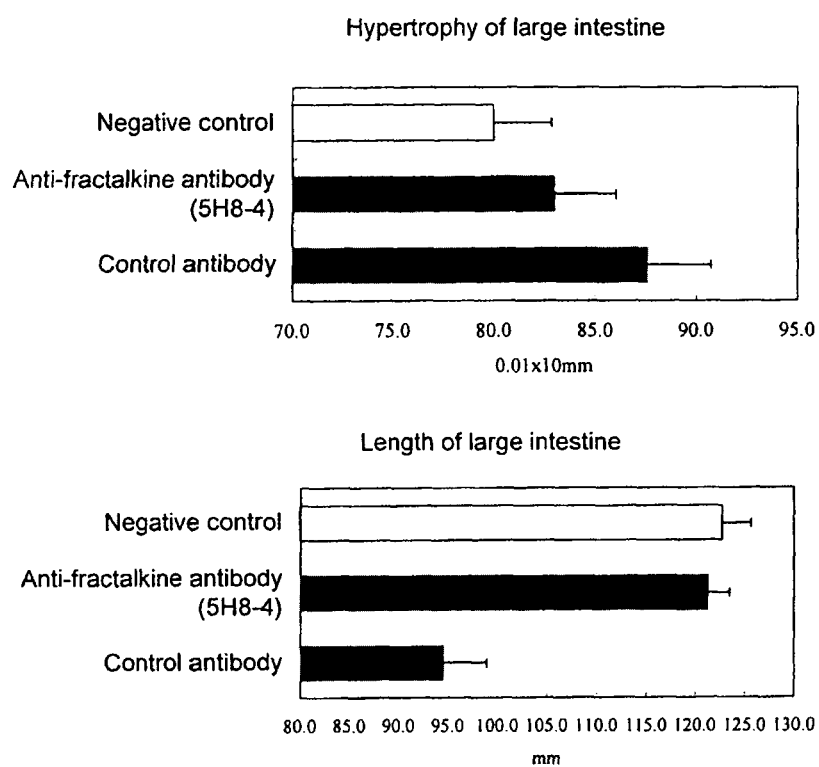
FIG. 7 It shows effect of the anti-mouse fractalkine antibody (5H8-4) for improving large intestine hypertrophy and large intestine shortening in a mouse oxazolone-induced inflammatory bowel disease model.
Figure 8:
FIG. 8 It shows effect of the anti-mouse fractalkine antibody (5H8-4) for improving morphological changes in the large intestine in a mouse oxazolone-induced inflammatory bowel disease model (photographs of organ morphology).
Figure 8:
Figure 8:
Figure 9:
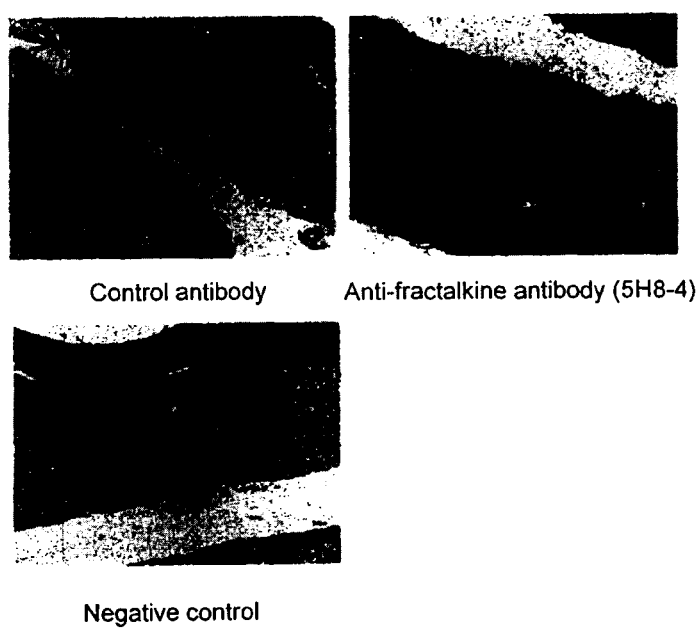
FIG. 9 It shows effect of the anti-mouse fractalkine antibody (5H8-4) for improving large intestine tissue damage in a mouse oxazolone-induced inflammatory bowel disease model (microphotographs).

Compared with the control antibody administration group, the anti-fractalkine antibody (5H8-4) administration group showed improved DAI from the second days after the intestinal injection of oxazolone (FIG. 6). Further, hypertrophy and shortening of the large intestine also improved in the anti-fractalkine antibody (5H8-4) administration group compared with the control antibody administration group (FIG. 7). In the morphological observation of the large intestine sites, hypertrophy was observed at sites from the colon to the rectum in the control antibody administration group, but improvement was observed by administration of the anti-fractalkine antibodies (5H8-4) (FIG. 8). In the tissue section staining, a very large number of leukocytes (T lymphocytes, monocytes, macrophages etc.) infiltrated into the large intestine mucosal layer, and disappearance of goblet cells producing mucus, and damage and hypertrophy were observed in the large intestine epithelial tissues in the control antibody group. In contrast, in the anti-fractalkine antibody (5H8-4) administration group, leukocyte infiltration was inhibited, and large intestine epithelial cells were hardly damaged (FIG. 9). It was expected from the above results that the fractalkine-CX3CR1 cell infiltration system played an important role also in the oxazolone-induced colitis model, and it was suggested that the fractalkine-CX3CR1 cell infiltration system was a useful treatment system for inflammatory bowel diseases.

Example 3

Effect of Anti-Fractalkine Antibody (#126) in Mouse Oxazolone-Induced Inflammatory Bowel Disease Model (1) Preparation of Anti-Fractalkine Antibody (#126)

Mouse fractalkine (Genzyme) and Titer Max™ Gold adjuvant were mixed, and then used to immunize Armenian hamsters two or more times, and the final immunization was further performed with the mouse fractalkine alone. The antibody titer in the serum was measured by ELISA using solid-phased fractalkine, and lymphocytes were isolated from Armenian hamsters in which the antibody titer increased. The lymphocytes and P3 myeloma cells were mixed at a ratio of 5:1, and cell fusion was performed by using PEG (Rosh). The hybridomas were cultured on a plate for one week by using RPMI-1640/10% FCS/HAT/10% Origen HCF (ISGN). Then, the culture supernatant was assayed by ELISA using solid-phased fractalkine to identify positive wells. The hybridomas producing the anti-fractalkine antibodies were cloned by performing limiting dilution twice. By using a protein A column, the monoclonal antibodies were purified from the ascites prepared by inoculating the hybridoma to SCID and nude mice to which pristine was administered. The neutralization activity of the obtained antibodies was determined by using inhibition of migration of CX3CR1 expressing cells to mouse fractalkine as an index, and the #126 antibody having neutralization activity was obtained. The hybridoma producing the neutralizing antibody was designated as Ham @mFKN#126.1.1.

(2) Method

Investigation was performed in the same manner as that used in Example 2. The evaluation items were large intestine shortening and hypertrophy. To seven mice in each group given with intestinal injection of oxazolone, 500 μg of a control antibody (hamster IgG) or 500 μg of the anti-fractalkine antibody (#126) (antibody in PBS) was administered.

(3) Results

Figure 10:
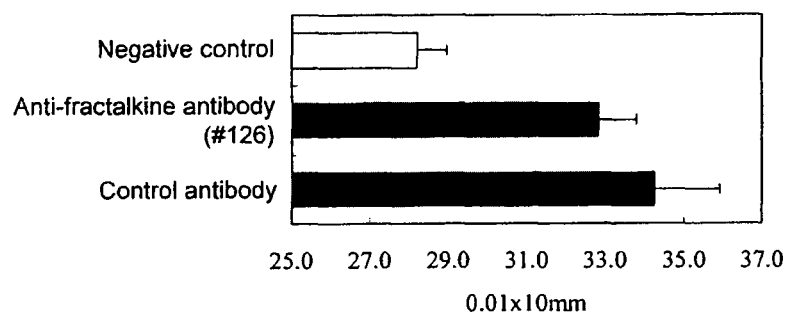
FIG. 10 It shows effect of the anti-mouse fractalkine antibody (#126) for improving large intestine hypertrophy and large intestine shortening in a mouse oxazolone-induced inflammatory bowel disease model.
Figure 10:
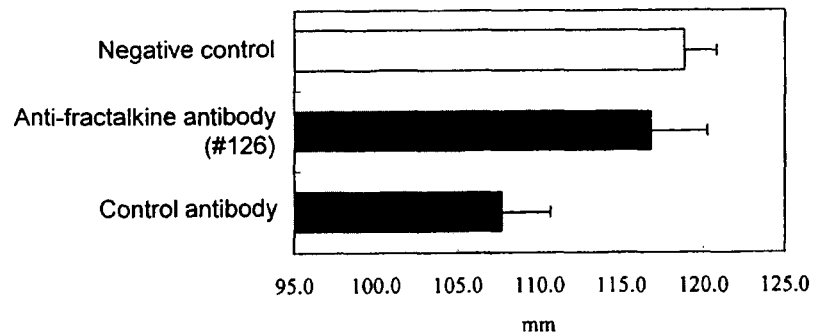

Like the 5H8-4 anti-fractalkine antibody, the #126 anti-fractalkine antibody improved large intestine shortening and hypertrophy compared with the control antibody (FIG. 10). These results strongly suggested that inhibition of the fractalkine-CX3CR1 cell infiltration system was useful for treatment of inflammatory bowel disease since two different types of anti-fractalkine antibodies exhibited effects in the oxazolone-induced colitis model.

Example 4

Expression of iNOS in ConA-Induced Hepatitis and Effect of Anti-Fractalkine Antibody (5H8-4) on iNOS Production (1) Method To four C57BL/6 mice mouse in each group, 500 μg of a control antibody (hamster IgG) or 500 μg of the anti-fractalkine antibody (5H8-4) (antibodies in PBS) was intravenously administered, and then immediately 12 mg/kg of concanavalin A (ConA, Sigma Aldrich) was intravenously administered. The liver was removed two hours later, and RNA was extracted. As a negative control group, there were provided four C57BL/6 mice to which PBS (phosphate buffer) was intravenously administered. The expression of mRNA for iNOS was measured by collecting RNA, synthesizing cDNA, and measuring it by real time PCR in the same manner as that used in Example 1. Further, 12 hours after the intravenous administration of the control antibody or the anti-fractalkine antibody and ConA, or PBS for the negative control group, the liver was removed, and frozen tissue sections were prepared. Immunohistologic staining was performed with the anti-iNOS antibodies and the anti-CX3CR1 antibodies, and iNOS and CX3CR1-positive cells were counted.

(2) Results

Figure 11:
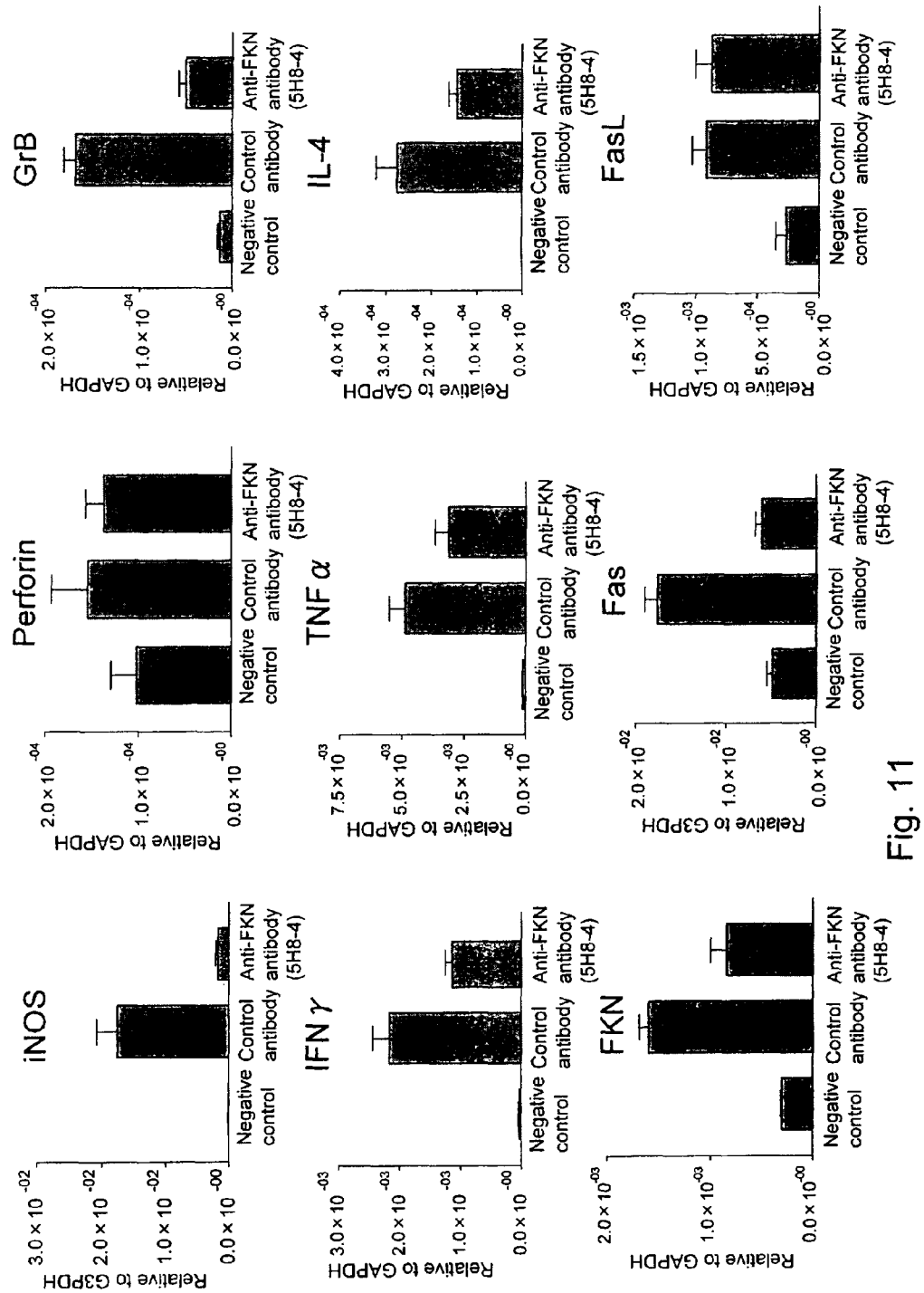
FIG. 11 It shows effect of the anti-mouse fractalkine antibody (5H8-4) for improving expressions of various factors in liver tissue in ConA-induced hepatitis.
Figure 12:
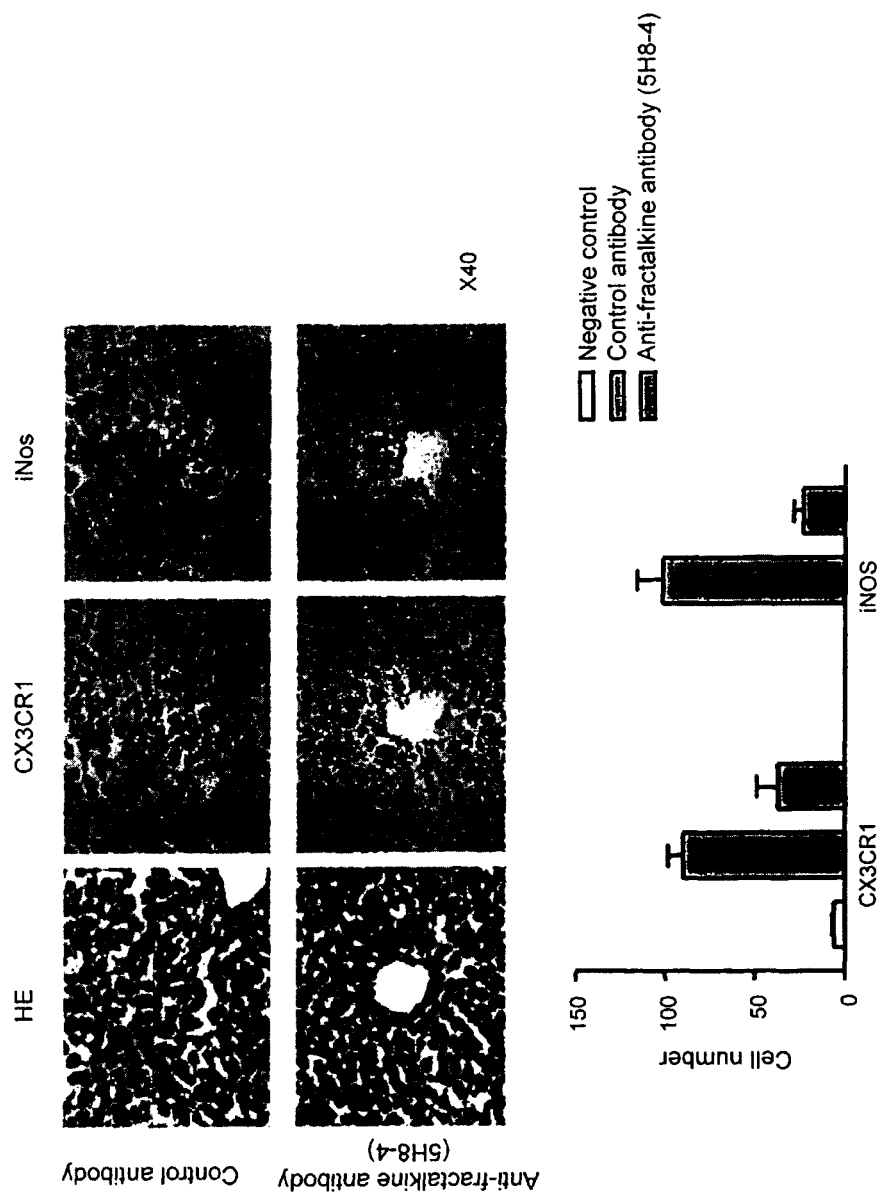
FIG. 12 It shows effect of the anti-mouse fractalkine antibody (5H8-4) for improving increases in iNOS and CX3CR1-positive inflammatory cells in the liver parenchyma in ConA-induced hepatitis (microphotographs).

The expression of mRNA for iNOS increased by the administration of ConA was markedly decreased by the administration of the anti-fractalkine antibody. Further, expressions of mRNAs for cytotoxic factors such as granzyme B and Fas and cytokines such as IFNγ, TNFα and IL-4 were increased by the administration of ConA, and these expressions were decreased by the administration of the anti-fractalkine antibody (5H8-4) (FIG. 11). Further, the results of immunohistologic staining showed that iNOS positive inflammatory cells were increased by the administration of ConA, and markedly decreased by the administration of the anti-fractalkine antibody (FIG. 12). Further, CX3CR1-positive inflammatory cells were also increased by the administration of ConA, and markedly decreased by the administration of the anti-fractalkine antibody (5H8-4) (FIG. 12). The above results revealed that, by inhibiting the interaction of fractalkine and CX3CR1, expression of mRNA for iNOS was inhibited in the liver of ConA-induced hepatitis, and the iNOS production was inhibited in inflammatory cells, and thus it was suggested that tissue damage in the liver was ameliorated by inhibition of excessive NO production by inflammatory cells.

Example 5

Analysis of CX3CR1 and iNOS Expressing Cells in ConA-Induced Hepatitis

The results of immunohistologic staining were analyzed in detail. Most of the CX3CR1-positive cells were small and round, and had a horseshoe-shaped nucleus and a small amount of cytoplasm. They existed adjacent to the portal vein, central vein and sinusoid, and a part of them were observed also in the peripheries of necrotic regions. Most of the iNOS-positive cells were largely extended, and had a horseshoe-shaped nucleus and a large amount of cytoplasm. They existed adjacent to the sinusoid and were also observed in necrotic regions in addition to their peripheries, but not in the vicinity of the portal vein or central vein. Since differences were observed between CX3CR1-positive cells and iNOS-positive cells in their morphology and localization as described above, characteristics of CX3CR1-positive cells and iNOS-positive cells were analyzed in detail.

(1) Method

In the same manner as that used in Example 4, frozen tissue sections were prepared by using the liver obtained 12 hours after intravenous administration of ConA (ConA-induced hepatitis liver tissue). Double fluorescence staining was performed with the anti-CX3CR1 antibody or the anti-iNOS antibody (BD Bioscience) and the anti-BM8 antibody (BMA), the anti-CD11b antibody (eBioscience) or the anti-MCP-1 antibody (Gengyme Techne), and BM8, CD11b and MCP-1 positive rates in the CX3CR1-positive cells and iNOS-positive cells were measured.

The aforementioned anti-CX3CR1 antibody was prepared in rabbits by using a mouse CX3CR1C-terminus peptide (CSILSSFTHYTSEGDGSLLL (SEQ ID NO: 31)) as an antigen. Specifically, they were obtained as follows. A synthetic peptide of SEQ ID NO: 31 was bound to KLH, and used to immunize rabbits (JW) in an amount of 250 μg/rabbit at one time with an adjuvant. As the adjuvant, the complete Freund's adjuvant was used only for the initial immunization, and the incomplete Freund's adjuvant was used for the other remaining immunizations. The immunization was performed five times in total. The increase in the antibody titer was confirmed by ELISA by using a solid-phased peptide, and the serum was collected. Affinity purification was performed by using the peptide having the aforementioned sequence bound to Thiopropyl Sepharose 4B (Amersham Bioscience) to obtain the anti-CX3CR1 antibody from the collected serum.

Further, CX3CR1-positive cells in the peripheral blood (PBL) and bone marrow cells of 9-week old male C57BL/6 mice were cultured with M-CSF (50 ng/ml) for five days, and CX3CR1-positive cells among macrophages (BMMφ) differentiated from the bone marrow cells were analyzed by flow cytometry (FACS) for F4/80 specific to macrophages and monocytes and Ly6C, a surface marker of immature bone marrow system cells, by using anti-F4/80 antibody (CAL-TAG) and anti-Ly6C antibody (BMA). Further, tissue staining of ConA-induced hepatitis liver tissues with the anti-Ly6C antibody and tissue staining of ConA-induced hepatitis liver tissues infiltrated with fluorescence-labeled macrophages with the anti-MCP-1 antibody were performed.

(2) Results

Figure 13:
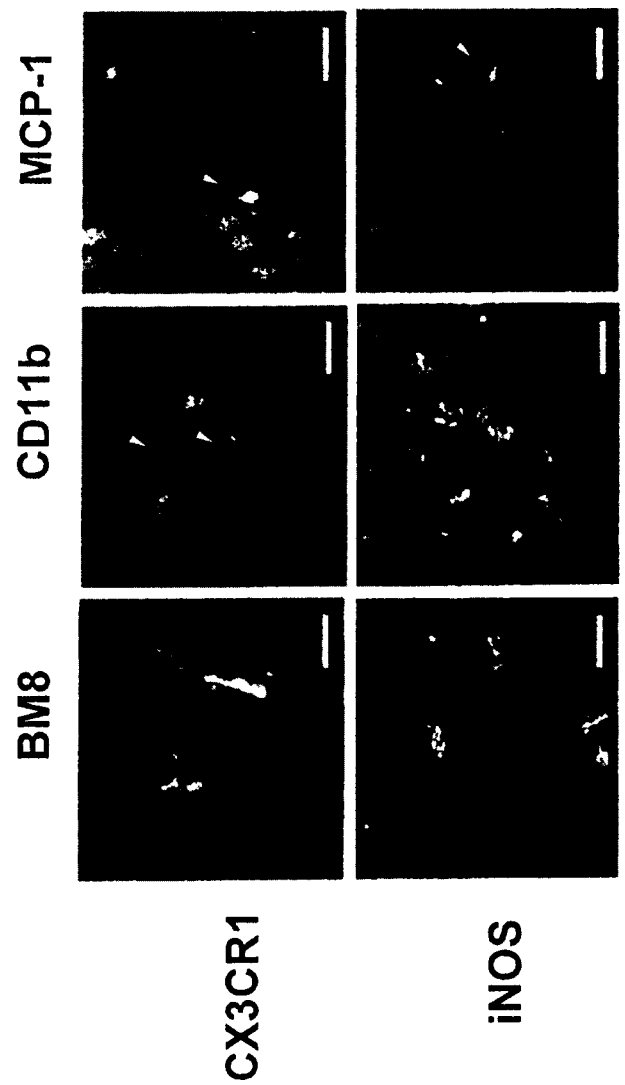
FIG. 13 It shows results of double fluorescence staining of liver tissues in ConA-induced hepatitis (microphotographs).
Figure 14:
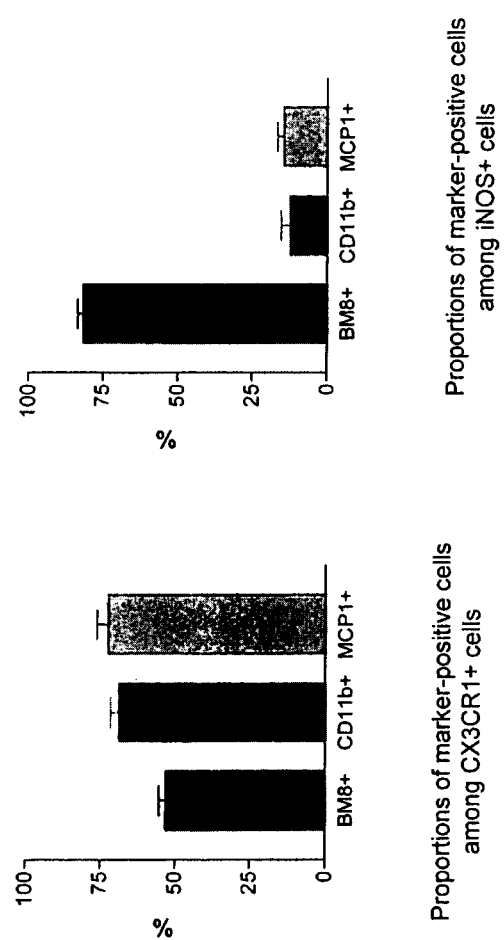
FIG. 14 It shows proportions of marker-positive cells among CX3CR1-positive cells and iNOS-positive cells in liver tissues in ConA-induced hepatitis.

Representative staining images are shown in FIG. 13. In the figure, letters at the left and top of the photographs represent the markers recognized by the antibodies used in the fluorescence staining. The length of the bar is 20 μm. The measurement results for the positive rate of each marker are shown in FIG. 14. In the figure, BM8+ denotes BM8 positive, CD11b+ denotes CD11b positive, and MCP1+ denotes MCP-1 positive.

The CX3CR1-positive cells comprised 68.9±2.7% (n=3) of small and round CD11b-positive cells, and 53.4±2.0% (n=3) of large and extended BM8-positive cells. On the other hand, the iNOS-positive cells comprised 81.6±1.8% (n=3) of large and extended BM8-positive cells, and 12.6±3.0% (n=3) of CD11b-positive cells. Therefore, it was revealed that the CX3CR1-positive cells were not necessarily iNOS-positive cells, and a part of them were expressed in another cell group. It has been recently reported that CCR2 is involved in infiltration of iNOS producing cells in a bacterial infection model mouse (Non-patent document 13). Accordingly, expression of MCP-1, a ligand of CCR2, was analyzed. MCP-1-positive cells were small and round like the CX3CR1-positive cells. MCP-1 was expressed in 72.5±3.7% (n=3) of the CX3CR1-positive cells, and most of the MCP-1-positive cells were CX3CR1-positive. Therefore, it was revealed that the CX3CR1-positive cells were major cells among the cells expressing MCP-1 in ConA-induced hepatitis. Further, as expected from the morphological differences between the MCP-1-positive cells and iNOS-positive cells, MCP-1 was expressed in only 14.6±2.2% (n=3) of the iNOS-positive cells, and they were hardly overlapped with each other. Therefore, it was found that most of the iNOS-positive cells were not CX3CR1/MCP-1-positive cells. Interestingly, iNOS-positive cells and MCP-1-positive cells existed adjacent to each other at a high frequency in the sinusoidal vessels and necrotic lesions in the liver.

Figure 15:
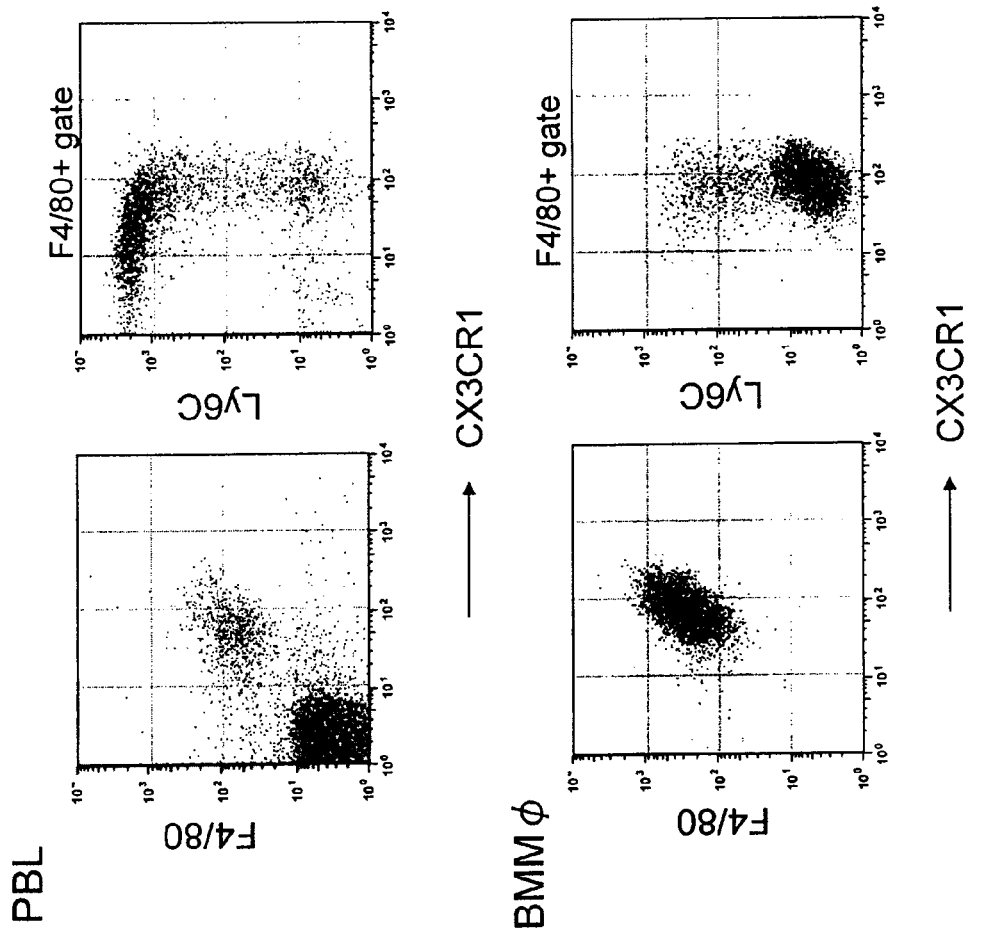
FIG. 15 It shows results of flow cytometry of CX3CR1-positive cells.
Figure 16:
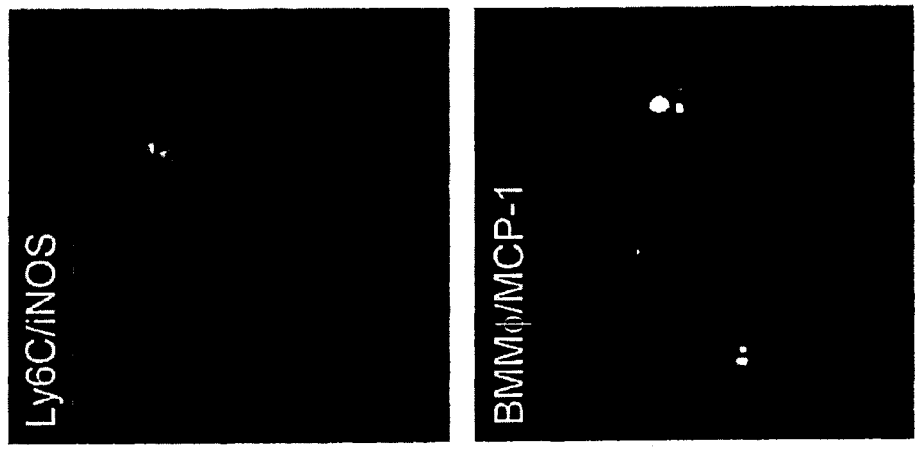
FIG. 16 It shows results of histological staining of liver tissues in ConA-induced hepatitis (microphotographs).

The results of the analysis of CX3CR1-positive cells based on FACS are shown in FIG. 15. The results of the tissue staining are shown in FIG. 16.

As a result of the analysis of the CX3CR1-positive cells by FACS using peripheral blood (PBL), CX3CR1 was expressed in the F4/80-positive monocytes, and the expression level was high in the Ly6C– mature monocytes and low in the Ly6C+ immature monocytes. As a result of the tissue staining of the liver obtained 12 hours after the administration of ConA with Ly6C, which is a surface marker of immature bone marrow system cells, it was suggested that iNOS-positive and F4/80-positive cells were Ly6C-positive, and were derived from immature monocytes. Subsequently, bone marrow cells of 9-week old male C57BL/6 mice were cultured with M-CSF (50 ng/ml) for five days to obtain macrophages (BMMφ) differentiated from bone marrow cells. The adhered BMMφ macrophages were collected with 1 mM EDTA/PBS and analyzed by FACS. As a result, they were CX3CR1hi F4/80+ Ly6C–/low like the peripheral blood mature monocytes. Then, BMMφ macrophages were labeled with fluorescence by using 10 μM CFSE, $2.5 \times 10^6$ cells/250 μl were intravenously injected to mice, ConA (15 mg/kg) was further intravenously injected ten minutes later, and the liver was collected 12 hours later for examination of infiltration.

Infiltration of BMMφ to the liver was markedly increased by the administration of ConA. Further, the infiltrated fluorescence-labeled cells produced MCP-1 because of the administration of ConA. iNOS was not expressed in the fluorescence-labeled cells and derived from the host.

The above results suggested that CX3CR1-positive mature monocytes infiltrated into the inflammation sites upon inflammation to express MCP-1 and induce infiltration of iNOS producing immature monocytes into the inflammation sites, and thereby cause pathological conditions.

Example 6

Expressions of Chemokines in ConA-Induced Hepatitis and Effect of Anti-Fractalkine Antibody (5H8-4) on Expressions of Chemokines (1) Method Expressions of mRNAs for chemokines were measured by real time PCR in the same manner as that used in Example 1 by using cDNA derived from the liver two hours after intravenous administration of ConA prepared in Example 4. The primer sets used were as follows. The glyceraldehyde-3-phosphate dehydrogenase (G3PDH) gene was used as a control gene.

TABLE 4

| Primer | Sequence | SEQ ID NO: |
|---|---|---|
| mMCP-1 sense | 5'-AGGTCCCTGTCATGCTTCTG-3' | 19 |
| mMCP-1 anti-sense | 5'-TCATTGGGATCATCTTGCTG-3' | 20 |
| mKC sense | 5'-CTTGAAGGTGTTGCCCTCAG-3' | 21 |
| mKC anti-sense | 5'-TGGGGACACCTTTTAGCATC-3' | 22 |
| mMIP-2 sense | 5'-TCCAGAGCTTGAGTGTGACG-3' | 23 |
| mMIP-2 anti-sense | 5'-GCCTTGCCTTTGTTCAGTATC-3' | 24 |
| mIP-10 sense | 5'-TGAATCCGGAATCTAAGACCA-3' | 25 |
| mIP-10 anti-sense | 5'-GAGGCTCTCTGCTGTCCATC-3' | 26 |
| mMIP-1α sense | 5'-ACCATGACACTCTGCAACCA-3' | 27 |
| mMIP-1α anti-sense | 5'-GATGAATTGGCGTGGAATCT-3' | 28 |

TABLE 4-continued

| Primer | Sequence | SEQ ID NO: |
|---|---|---|
| mMIP-1β sense | 5'-CCCACTTCCTGCTGTTTCTC-3' | 29 |
| mMIP-1β anti-sense | 5'-CTCACTGGGGTTAGCACAGA-3' | 30 |

(2) Results

Figure 17:
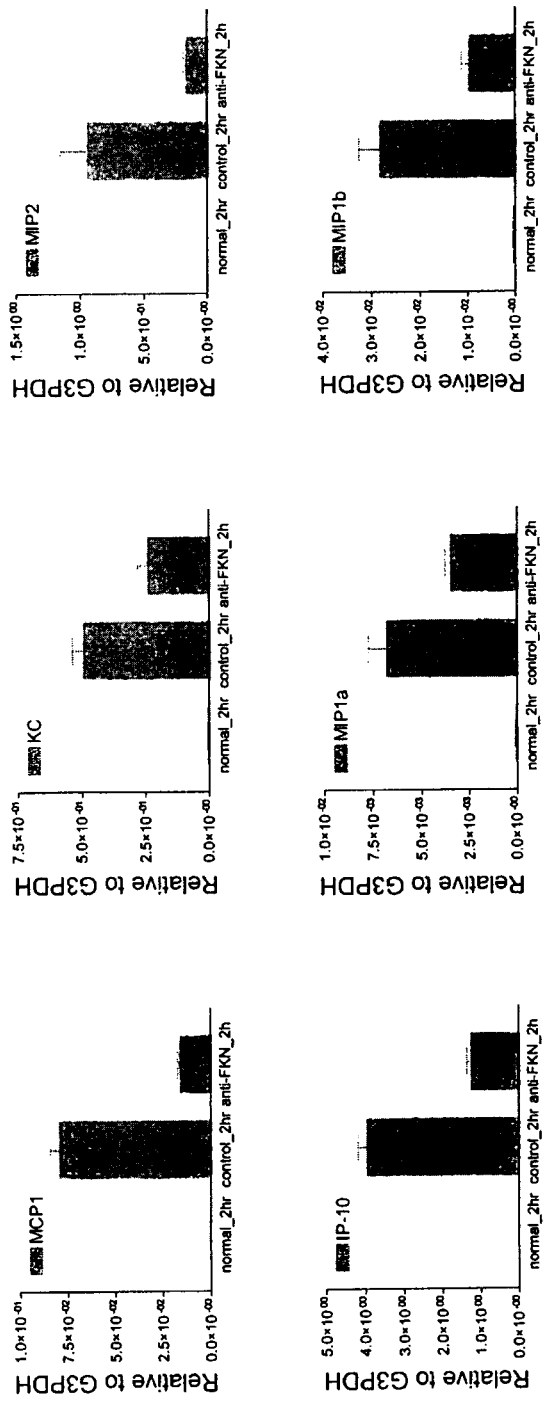
FIG. 17 It shows expressions of chemokines in ConA-induced hepatitis and effect of the anti-fractalkine antibody (5H8-4) on expressions of chemokines.

The results are shown in FIG. 17. In the figure, "normal" denotes a negative control, "control" denotes a control antibody administration group, and "anti-FKN" denotes an anti-fractalkine administration group.

Two hours after the administration of ConA, expressions of mRNAs for MCP-1, KC, MIP-2, IP-10, MIP-1α and MIP-1β increased in the liver. The expressions of mRNAs for these chemokines were decreased by the administration of the anti-fractalkine antibody. These results suggested that production of many types of chemokines was inhibited by inhibition of the interaction of fractalkine and CX3CR1, and thus the amplifying pathway of inflammatory cell infiltration and activation as the initial inflammation induction reactions extensively became not to function.

Example 7

Expressions of mRNAs for Cell Surface Markers, Cytokines, Chemokines, Cell Activation Molecules and Cytotoxic Molecules and Effect of Anti-Fractalkine Antibody (5H8-4) on Expressions of mRNAs for Cell Surface Markers, Cytokines, Chemokines, Cell Activation Molecules and Cytotoxic Molecules in Mouse Inflammatory Bowel Disease Model Transfused with CD4-Positive and CD45RB Strongly-Positive (CD4$^+$CD45RB$^{high}$) T Lymphocytes (1) Method Expressions of mRNAs for leukocyte markers, cytokines, chemokines and molecules involved in cell activation and tissue destruction were measured in more detail by TaqMan PCR in the same manner as that used in Example 1 using cDNA derived from the large intestine prepared in Example 1. The primer sets used were as follows.

TABLE 5

| Primer | Sequence | SEQ ID NO: |
|---|---|---|
| CD4 sense | 5'-GGGCTGTGGCAGTGTCTACT-3' | 32 |
| CD4 anti-sense | 5'-CTGGTTCACCCCTCTGGATA-3' | 33 |
| F4/80 sense | 5'-TGCCTCCCTGACTTTCAAAT-3' | 34 |
| F4/80 anti-sense | 5'-TGGCATTGCTGTATCTGCTC-3' | 35 |
| T-bet sense | 5'-GGGAAGCTAAAGCTCACCAA-3' | 36 |
| T-bet anti-sense | 5'-CCTCTGGCTCTCCATCATTC-3' | 37 |
| CD11c sense | 5'-CTTATCGTGGGCAGCTCAGT-3' | 38 |
| CD11c anti-sense | 5'-CCATTTGCTTCCTCCAACAT-3' | 39 |
| M-CSF receptor sense | 5'-CGACTTCTTCAAGTGACTCCTTC-3' | 40 |
| M-CSF receptor anti-sense | 5'-CTACGTCCCGGTGGATGC-3' | 41 |
| Ly-6G sense | 5'-GATGGATTTTGCGTTGCTCT-3' | 42 |
| Ly-6G anti-sense | 5'-GTCCAGAGTAGTGGGGCAGA-3' | 43 |
| IL-1β sense | 5'-GCTGAAAGCTCTCCACCTCA-3' | 44 |
| IL-1β anti-sense | 5'-AGGCCACAGGTATTTTGTCG-3' | 45 |
| IL-6 sense | 5'-CAAAGCCAGAGTCCTTCAGAG-3' | 46 |
| IL-6 anti-sense | 5'-GCCACTCCTTCTGTGACTCC-3' | 47 |
| IL-12α sense | 5'-GCCAGGTGTCTTAGCCAGTC-3' | 48 |
| IL-12α anti-sense | 5'-TCTTCAATGTGCTGGTTTGG-3' | 49 |
| IL-12β sense | 5'-ATCCAGCGCAAGAAAGAAAA-3' | 50 |
| IL-12β anti-sense | 5'-AATAGCGATCCTGAGCTTGC-3' | 51 |
| IL-23α sense | 5'-CAACAGCCAGTTCTGCTTGC-3' | 52 |
| IL-23α anti-sense | 5'-GATCCTCTGGCTGGAGGAG-3' | 53 |
| IL-17 sense | 5'-TCCAGAAGGCCCTCAGACTA-3' | 54 |
| IL-17 anti-sense | 5'-TGAGCTTCCCAGATCACAGA-3' | 55 |
| RANKL sense | 5'-CATTTGCACACCTCACCATC-3' | 56 |

TABLE 5-continued

| Primer | Sequence | SEQ ID NO: |
|---|---|---|
| RANKL anti-sense | 5'-TCCGTTGCTTAACGTCATGT-3' | 57 |
| KC sense | 5'-CTTGAAGGTGTTGCCCTCAG-3' | 58 |
| KC anti-sense | 5'-TGGGGACACCTTTTAGCATC-3' | 59 |
| MIP-2 sense | 5'-TCCAGAGCTTGAGTGTGACG-3' | 60 |
| MIP-2 anti-sense | 5'-GCCTTGCCTTTGTTCAGTATC-3' | 61 |
| MCP-1 sense | 5'-AGGTCCCTGTCATGCTTCTG-3' | 62 |
| MCP-1 anti-sense | 5'-TCATTGGGATCATCTTGCTG-3' | 63 |
| MCP-3 sense | 5'-CTGCTTTCAGCATCCAAGTG-3' | 64 |
| MCP-3 anti-sense | 5'-CCCAGGGACACCGACTACT-3' | 65 |
| CXCR2 sense | 5'-GCTCACAAACAGCGTCGTAG-3' | 66 |
| CXCR2 anti-sense | 5'-AGGGCATGCCAGAGCTATAA-3' | 67 |
| CCR2 sense | 5'-CTTTGCAACTGCCTCTTTCC-3' | 68 |
| CCR2 anti-sense | 5'-TTCCCAGGAAGAGGTTGAGA-3' | 69 |
| MIP-1α sense | 5'-ACCATGACACTCTGCAACCA-3' | 70 |
| MIP-1α anti-sense | 5'-GATGAATTGGCGTGGAATCT-3' | 71 |
| MIP-1β sense | 5'-CCCACTTCCTGCTGTTTCTC-3' | 72 |
| MIP-1β anti-sense | 5'-CTCACTGGGGTTAGCACAGA-3' | 73 |
| CCR5 sense | 5'-GCCAGAGGAGGTGAGACATC-3' | 74 |
| CCR5 anti-sense | 5'-GCCAGAGGAGGTGAGACATC-3' | 75 |
| TARC sense | 5'-TGCTTCTGGGGACTTTTCTG-3' | 76 |
| TARC anti-sense | 5'-CATCCCTGGAACACTCCACT-3' | 77 |
| MDC sense | 5'-TTCTTGCTGTGGCAATTCAG-3' | 78 |
| MDC anti-sense | 5'-GCAGGATTTTGAGGTCCAGA-3' | 79 |
| CCR4 sense | 5'-TGTCCTCAGGATCACTTTCAGA-3' | 80 |
| CCR4 anti-sense | 5'-AGCAGGAGAAGCCAATGAGA-3' | 81 |
| IP-10 sense | 5'-TGAATCCGGAATCTAAGACCA-3' | 82 |
| IP-10 anti-sense | 5'-GAGGCTCTCTGCTGTCCATC-3' | 83 |
| I-TAC sense | 5'-CAAGCAAGCTCGCCTCATA-3' | 84 |
| I-TAC anti-sense | 5'-GCATGTTCCAAGACAGCAGA-3' | 85 |
| CXCR3 sense | 5'-GTTCTGCTGGTCTCCAGAGG-3' | 86 |
| CXCR3 anti-sense | 5'-TGCCACCACCACTACCACTA-3' | 87 |
| CD40 sense | 5'-GTCGGCTTCTTCTCCAATCA-3' | 88 |
| CD40 anti-sense | 5'-GCATCCGGGACTTTAAACC-3' | 89 |
| CD40L sense | 5'-TGGATCTGTGCTTTTTGCTG-3' | 90 |
| CD40L anti-sense | 5'-CCTTCTCCTTTGTTGCATCTC-3' | 91 |
| CD80 sense | 5'-GCTGAACAGACCGTCTTCCT-3' | 92 |
| CD80 anti-sense | 5'-GTTTGCAGAGCCAGGGTAGT-3' | 93 |
| CD86 sense | 5'-TTCAGCAAAACCAAATGCAG-3' | 94 |
| CD86 anti-sense | 5'-TGCACTTCTTATTTCAGGCAAA-3' | 95 |
| Class II sense | 5'-TCTACACCTGCGTGGTTCAG-3' | 96 |
| Class II anti-sense | 5'-GCCAACACAGAAGATGATGAAG-3' | 97 |
| TLR2 sense | 5'-TAGGGGCTTCACTTCTCTGC-3' | 98 |
| TLR2 anti-sense | 5'-CCAAAGAGCTCGTAGCATCC-3' | 99 |
| bFGF sense | 5'-CCAACCGGTACCTTGCTATG-3' | 100 |
| bFGF anti-sense | 5'-GTGCCACATACCAACTGGAG-3' | 101 |
| VEGF Receptor 2 sense | 5'-CCAAGCTCAGCACACAGAAA-3' | 102 |
| VEGF Receptor 2 anti-sense | 5'-TCAGAATCACGCTGAGCATT-3' | 103 |
| MMP-2 sense | 5'-CCCCTGATGTCCAGCAAGTA-3' | 104 |
| MMP-2 anti-sense | 5'-TGCGATGAGCTTAGGGAAAC-3' | 105 |
| MMP-9 sense | 5'-AGACGACATAGACGGCATCC-3' | 106 |
| MMP-9 anti-sense | 5'-GTGGTTCAGTTGTGGTGGTG-3' | 107 |
| MMP-14 sense | 5'-CTGGGAAGGAATCCCTGAAT-3' | 108 |
| MMP-14 anti-sense | 5'-CTGGGAAGGAATCCCTGAAT-3' | 109 |

(2) Results

Figure 18:
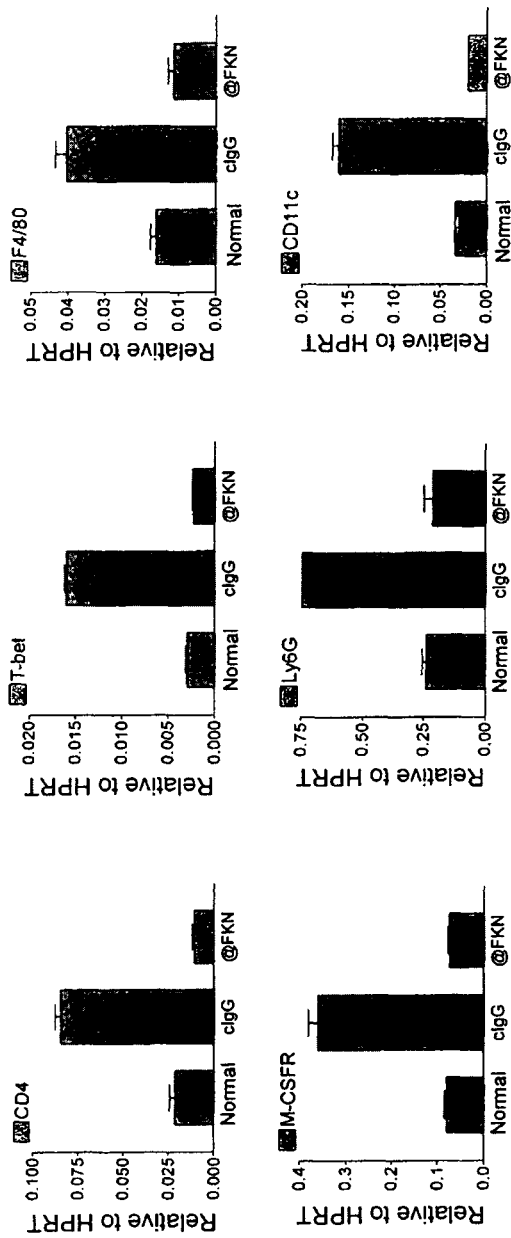
FIG. 18 It shows effect of the anti-mouse fractalkine antibody (5H8-4) for improving expressions of mRNAs for leukocyte markers in a mouse inflammatory bowel disease model transfused with CD4-positive and CD45RB strongly-positive T lymphocytes. "Normal" denotes a negative control, "cIgG" denotes the control antibody administration group, and "@FKN" denotes the anti-fractalkine antibody administration group (the same shall apply to FIGS. 19 to 25).
Figure 19:
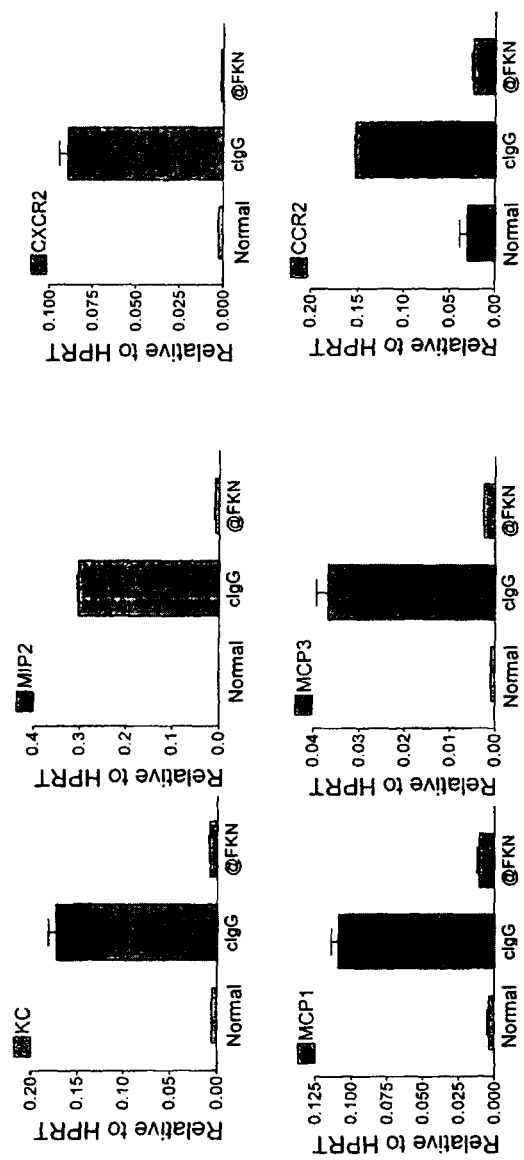
FIG. 19 It shows effect of the anti-mouse fractalkine antibody (5H8-4) for improving expressions of mRNAs for chemokines and chemokine receptors in a mouse inflammatory bowel disease model transfused with CD4-positive and CD45RB strongly-positive T lymphocytes.
Figure 20:
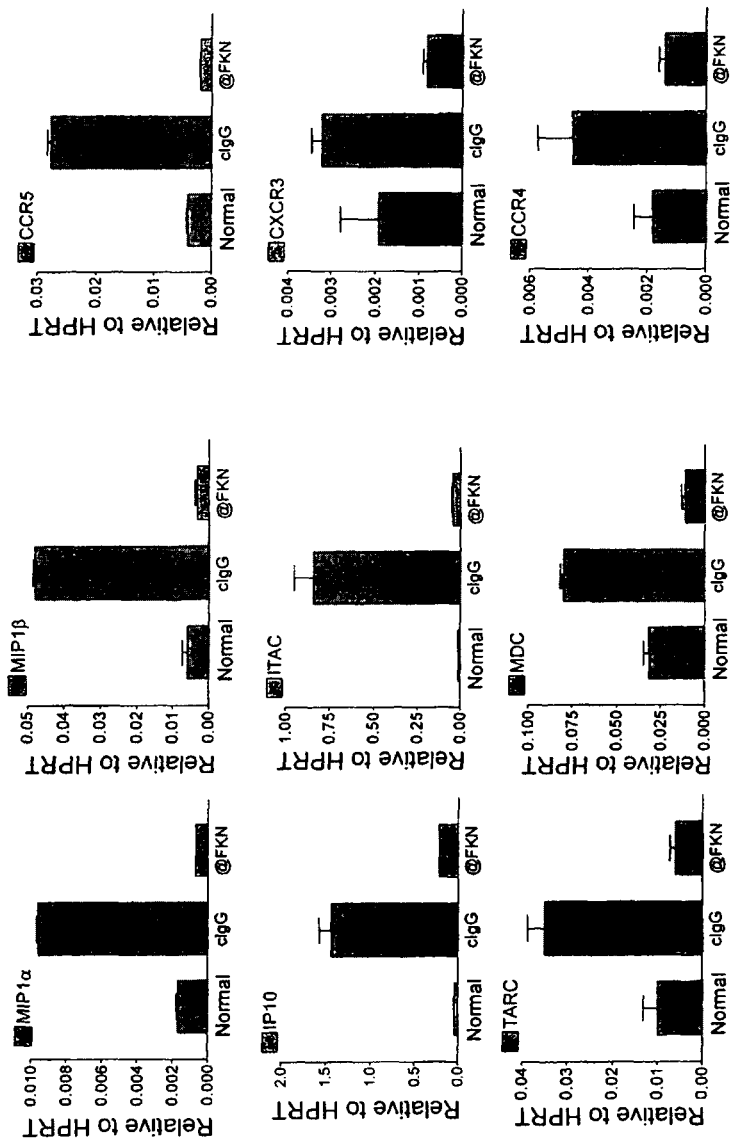
FIG. 20 It shows effect of the anti-mouse fractalkine antibody (5H8-4) for improving expressions of mRNAs for chemokines and chemokine receptors in a mouse inflammatory bowel disease model transfused with CD4-positive and CD45RB strongly-positive T lymphocytes.
Figure 21:
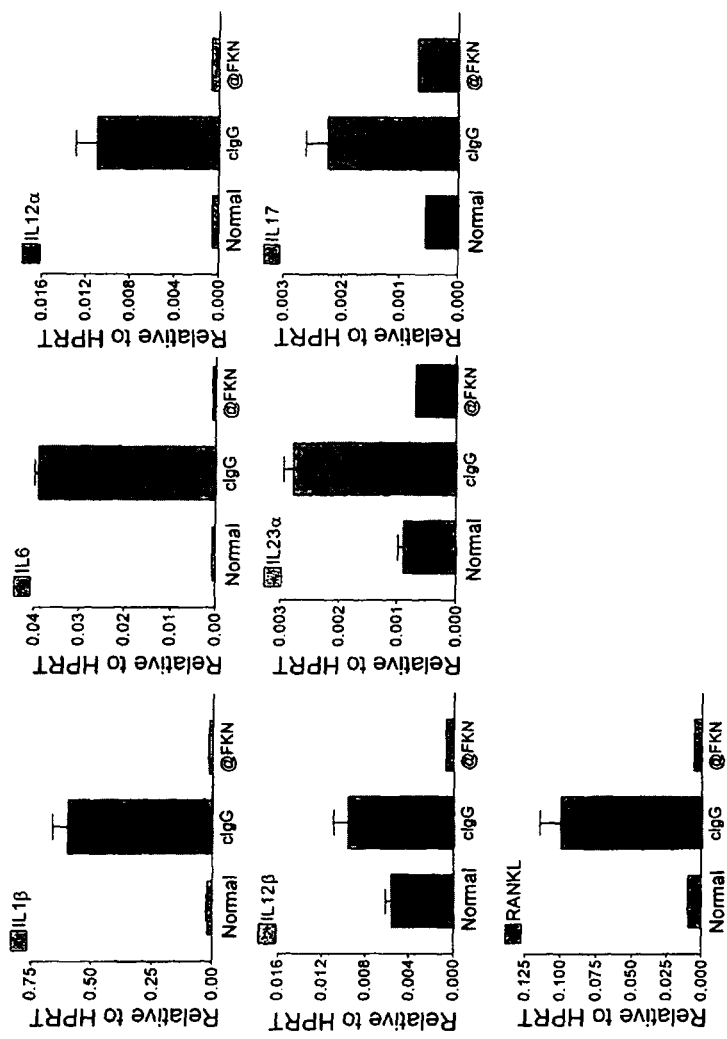
FIG. 21 It shows effect of the anti-mouse fractalkine antibody (5H8-4) for improving expressions of mRNAs for cytokines in a mouse inflammatory bowel disease model transfused with CD4-positive and CD45RB strongly-positive T lymphocytes.
Figure 22:
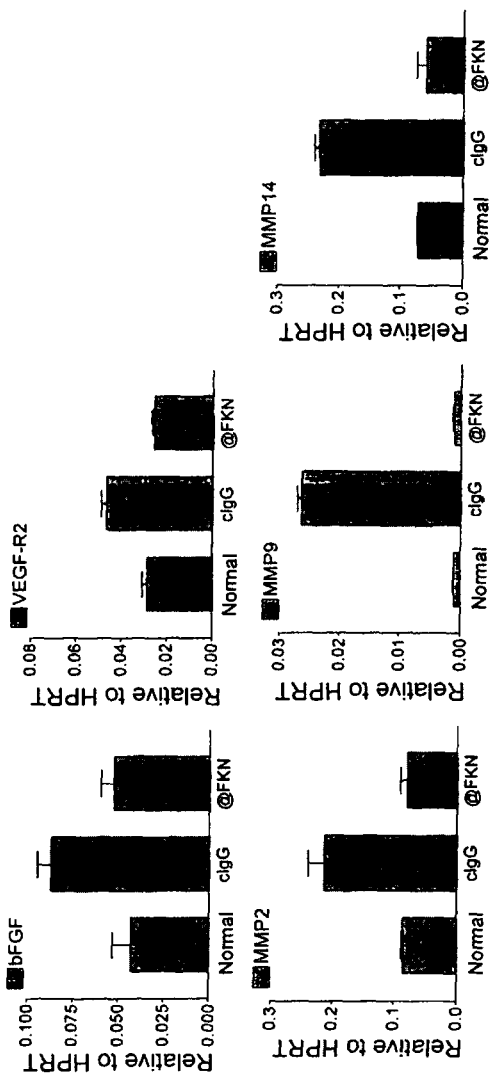
FIG. 22 It shows effect of the anti-mouse fractalkine antibody (5H8-4) for improving expressions of mRNAs for neovascularization molecules and tissue destroying proteases in a mouse inflammatory bowel disease model transfused with CD4-positive and CD45RB strongly-positive T lymphocytes.
Figure 23:
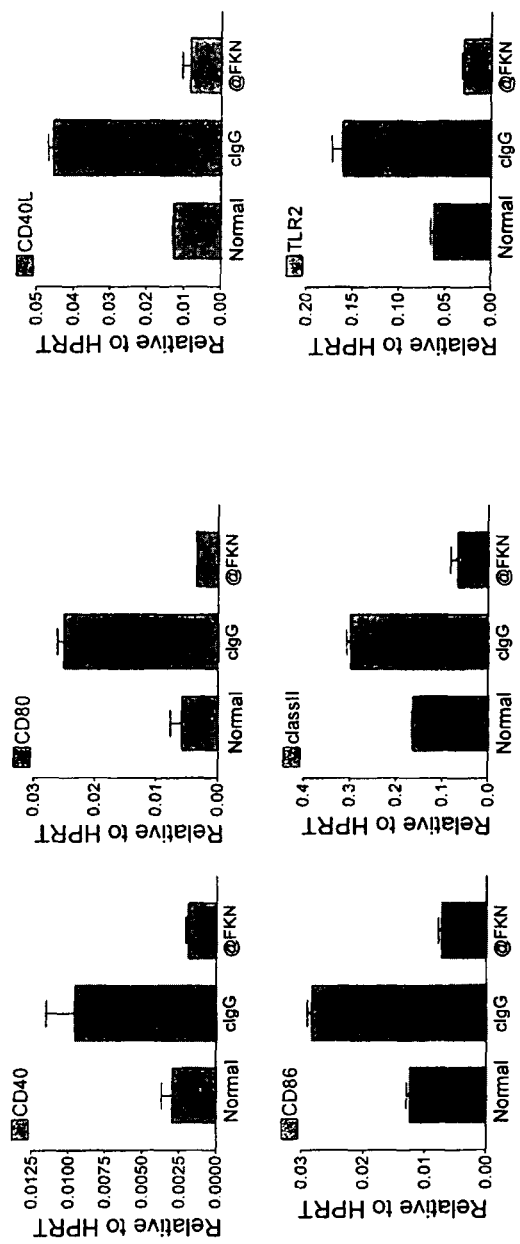
FIG. 23 It shows effect of the anti-mouse fractalkine antibody (5H8-4) for improving expressions of mRNAs for molecules activating dendritic cells and T cells in a mouse inflammatory bowel disease model transfused with CD4-positive and CD45RB strongly-positive T lymphocytes.

In the control antibody administration group, expressions of mRNAs for various leukocyte markers such as CD4, T-bet, F4/80, M-CSF receptor (M-CSF R), Ly-6G and CD11c increased (FIG. 18). These results suggested a possibility that the numerous infiltrated leukocytes in the control antibody administration group observed in the tissue section staining of Example 1 might be constituted by many types of leukocytes such as CD4+ T cells (in particular, Th1-type CD4+ T cells), monocytes/macrophages, neutrophils and dendritic cells. Further, since increases in expressions of mRNAs for chemokine-chemokine receptors such as KC, MIP-2, CXCR2, MCP-1, MCP-3, CCR2, MIP-1α, MIP-1β, CCR5, IP-10, I-TAC, CXCR3, TARC, MDC and CCR4 were observed in the control antibody administration group, it was inferred that the infiltrated leukocytes infiltrated via these chemokine-chemokine receptor mechanisms (FIGS. 19 and 20). Further, marked increases were also observed in expressions of mRNAs for a series of inflammatory cytokines such as IL-1β, IL-6, IL-12α, Il-12β, Il-23α, Il-17 and RANKL, proteases MMP-2, MMP-9 and MMP-14 involved in tissue destruction and further bFGF and VEGF Receptor 2 involved in neovascularization at inflammation sites in the control antibody administration group (FIGS. 21 and 22). Furthermore, since increases were observed in expressions of CD40 and TLR2, activation receptors of dendritic cells and so forth, CD40L, a molecule that is expressed in activated T cells and activates dendritic cells and so forth, molecules of T cell activation cosignal molecule group such as CD80 and CD86, of which expression is enhanced by activation of dendritic cells, and MHC Class II, a possibility was suggested that antigen-presenting cells such as T cells and dendritic cells were activated at lesion sites, and antigen-specific acquired immunity systems might be operating (FIG. 23). The expressions of mRNAs for the series of leukocyte markers, chemokine-chemokine receptors, cytokines, tissue destruction molecules, neovascularization related molecules and T cell/dendritic cell activation molecules were markedly inhibited by the administration of the anti-fractalkine antibodies (FIGS. 18 to 23). The above results suggested a possibility that by inhibition of the interaction of fractalkine and CX3CR1, production of inflammatory cytokines and chemokines was inhibited, thus the amplifying pathway of inflammatory cell infiltration and activation extensively became not to operate, and progression of pathological conditions in inflammatory bowel disease was prevented.

Example 8

Expressions of mRNAs for Cell Surface Markers, Cytokines, Chemokines, Cell Activation Molecules and Cytotoxic Molecules and Effect of Anti-Fractalkine Antibody (5H8-4) on Expressions of mRNAs for Cell Surface Markers, Cytokines, Chemokines, Cell Activation Molecules and Cytotoxic Molecules in Mouse Oxazolone-Induced Inflammatory Bowel Disease Model (1) Method An inflammatory bowel disease model was prepared in the same manner as that used in Example 2. The control antibody and the anti-fractalkine antibody (5H8-4) were administered according to the method in Example 2. Autopsy was performed 24 hours and three days after the intestinal injection of oxazolone, the large intestine was removed, and then RNA was extracted from the large intestine tissues in the same manner as that used in Example 1. The negative control group was given intestinal injection of 50% ethanol/physiological saline. Expressions of mRNAs for cytokines and chemokines were measured by TaqMan PCR in the same manner as that used in Example 1 by extracting RNA and then synthesizing cDNA. The used primer sets are as follows.

TABLE 6

| Primer | Sequence | SEQ ID NO: |
|---|---|---|
| IL-1β sense | 5'-GCTGAAAGCTCTCCACCTCA-3' | 110 |
| IL-1β anti-sense | 5'-AGGCCACAGGTATTTTGTCG-3' | 111 |
| IL-6 sense | 5'-CAAAGCCAGAGTCCTTCAGAG-3' | 112 |
| IL-6 anti-sense | 5'-GCCACTCCTTCTGTGACTCC-3' | 113 |

TABLE 6-continued

| Primer | Sequence | SEQ ID NO: |
|---|---|---|
| Ly-6G sense | 5'-GATGGATTTTGCGTTGCTCT-3' | 114 |
| Ly-6G anti-sense | 5'-GTCCAGAGTAGTGGGGCAGA-3' | 115 |
| KC sense | 5'-CTTGAAGGTGTTGCCCTCAG-3' | 116 |
| KC anti-sense | 5'-TGGGGACACCTTTTAGCATC-3' | 117 |
| MIP-2 sense | 5'-TCCAGAGCTTGAGTGTGACG-3' | 118 |
| MIP-2 anti-sense | 5'-GCCTTGCCTTTGTTCAGTATC-3' | 119 |
| MCP-1 sense | 5'-GGTCCCTGTCATGCTTCTG-3' | 120 |
| MCP-1 anti-sense | 5'-TCATTGGGATCATCTTGCTG-3' | 121 |
| MIP-1α sense | 5'-ACCATGACACTCTGCAACCA-3' | 122 |
| MIP-1α anti-sense | 5'-GATGAATTGGCGTGGAATCT-3' | 123 |
| MIP-1β sense | 5'-CCCACTTCCTGCTGTTTCTC-3' | 124 |
| MIP-1β anti-sense | 5'-CTCACTGGGGTTAGCACAGA-3' | 125 |
| MCP-3 sense | 5'-CTGCTTTCAGCATCCAAGTG-3' | 126 |
| MCP-3 anti-sense | 5'-CCCAGGGACACCGACTACT-3' | 127 |
| CXCR2 sense | 5'-GCTCACAAACAGCGTCGTAG-3' | 128 |
| CXCR2 anti-sense | 5'-AGGGCATGCCAGAGCTATAA-3' | 129 |

(2) Results

Figure 24:
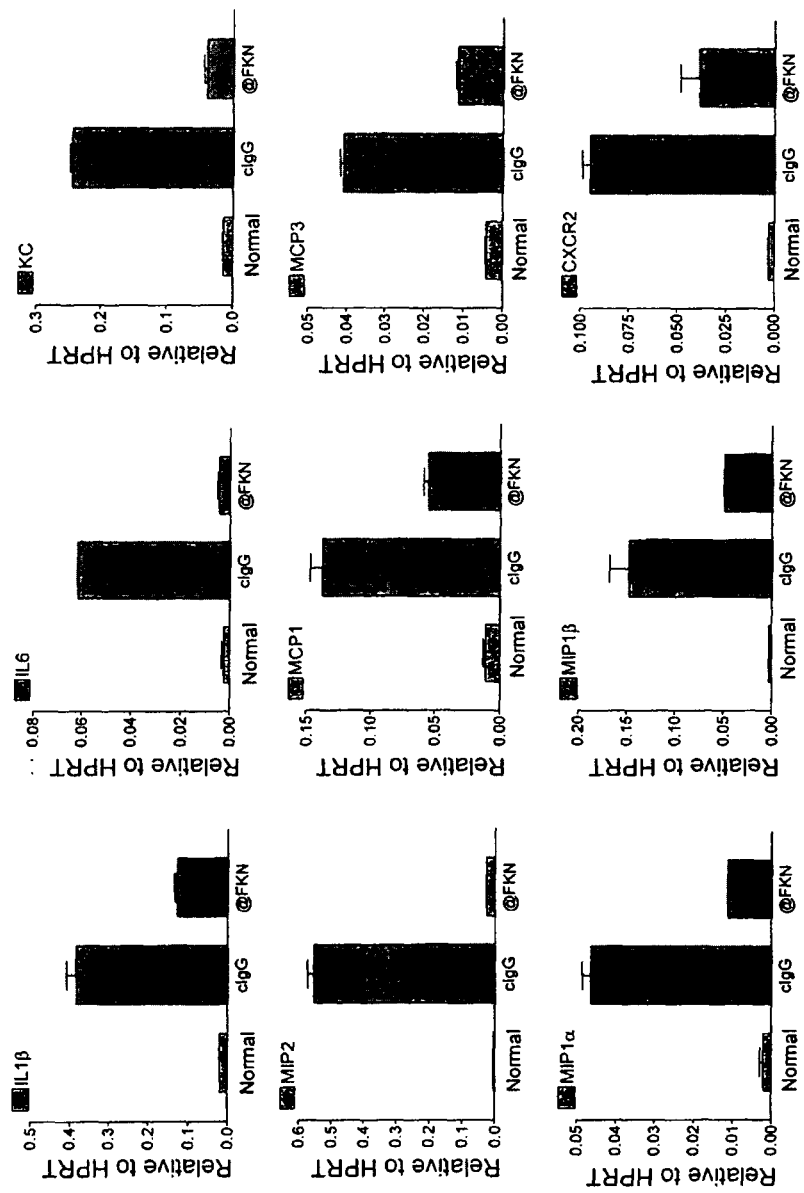
FIG. 24 It shows effect of the anti-mouse fractalkine antibody (5H8-4) for improving expressions of mRNAs for cytokines, chemokines and chemokine receptors 24 hours after intestinal injection of oxazolone in a mouse oxazolone-induced inflammatory bowel disease model.
Figure 25:
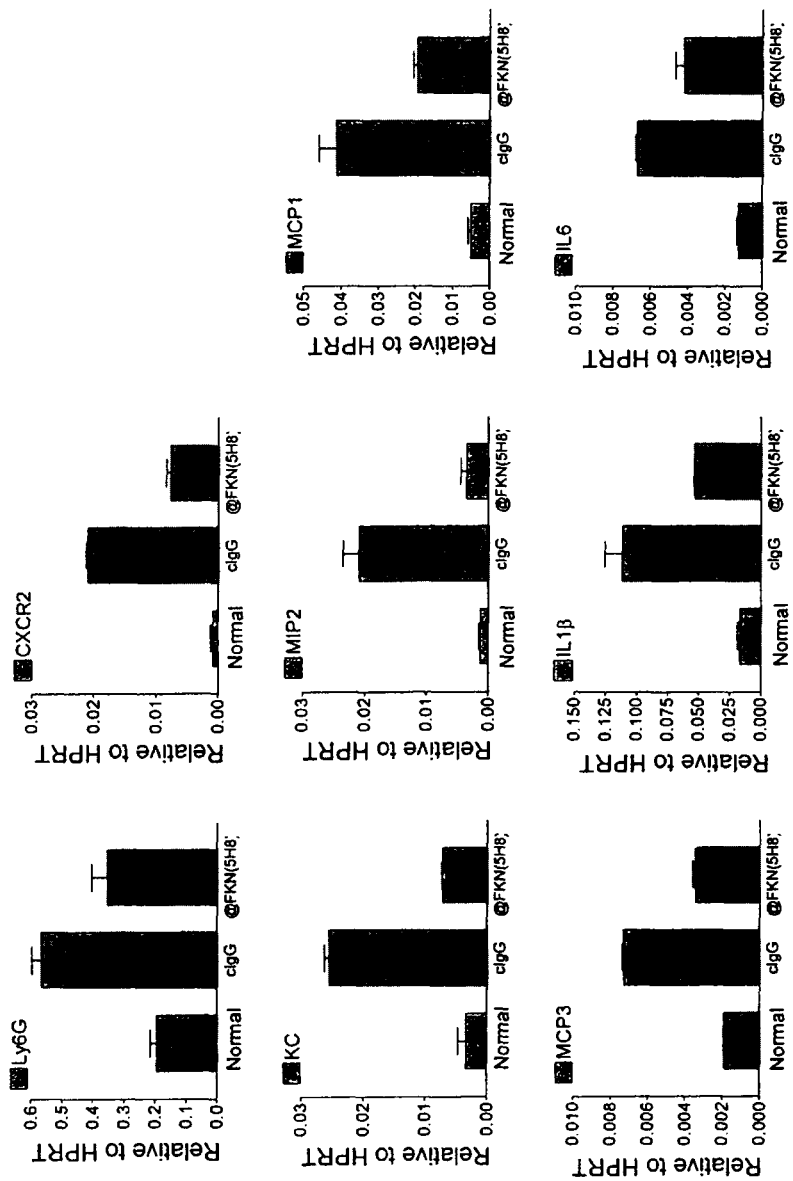
FIG. 25 It shows effect of the anti-mouse fractalkine antibody (5H8-4) for improving expressions of mRNAs for neutrophil markers, cytokines, chemokines and chemokine receptors three days after intestinal injection of oxazolone in a mouse oxazolone-induced inflammatory bowel disease model.

Twenty four hours after the intestinal injection of oxazolone, increases in expressions of mRNAs for inflammatory cytokines such as IL-1β and IL-6, chemokines such as KC, MIP-2, MCP-1, MCP-3, MIP-1α and MIP-1β and chemokine receptor CXCR2 were observed in the control antibody administration group, and these expression increases were markedly inhibited by the administration of the anti-fractalkine antibody (FIG. 24). Three days after the intestinal injection of oxazolone, an increase was observed in expression of mRNA for Ly-6G, a neutrophil marker, in addition to increases in expressions of mRNA for IL-1β, IL-6, KC, MIP-2, MCP-1, MCP-3 and CXCR2, and this increase in expression was markedly inhibited by administration of the anti-fractalkine antibody (FIG. 25). These results suggested that the pathological condition improving effect of the anti-fractalkine antibody in the oxazolone-induced inflammatory bowel disease model was exhibited partly by inhibition of production of the inflammatory cytokines and chemokines such as IL-1β and IL-6 or inhibition of infiltration of neutrophils.

INDUSTRIAL APPLICABILITY

There is provided a therapeutic agent for an inflammatory disease based on a novel approach, i.e., selective inhibition of excessive NO production by inhibition of iNOS activity in inflammatory cells.

The invention claimed is:

1. A method for treating an inflammatory bowel disease, the method comprising administering a therapeutically effective amount of an anti-fractalkine antibody to a subject in need thereof, wherein said anti-fractalkine antibody binds to fractalkine and inhibits an interaction of fractalkine and CX3CR1.

2. The method according to claim 1, wherein the anti-fractalkine antibody is a monoclonal antibody.

3. The method according to claim 2, wherein the anti-fractalkine antibody is a monoclonal antibody 5H8-4 produced by a hybridoma of the accession No. FERM BP-10372 or a monoclonal antibody #126 produced by a hybridoma of the accession No. FERM BP-10371.

4. The method according to claim 1, wherein the inflammatory bowel disease is ulcerative colitis or Crohn's disease.

5. The method according to claim 2, wherein the inflammatory bowel disease is ulcerative colitis or Crohn's disease.

6. The method according to claim 3, wherein the inflammatory bowel disease is ulcerative colitis or Crohn's disease.

7. The method according to claim 1, wherein the anti-fractalkine antibody is an antibody which recognizes an epitope which is recognized by a monoclonal antibody 5H8-4 produced by hybridoma of the accession No. FERM BP-10372 or a monoclonal antibody #126 produced by a hybridoma of the accession No. FERM BP-10371.

8. The method according to claim 7, wherein the inflammatory bowel disease is ulcerative colitis or Crohn's disease.

* * * * *